(12) United States Patent
Wessler et al.

(10) Patent No.: US 12,733,912 B2
(45) Date of Patent: Sep. 15, 2026

(54) SYSTEMS AND METHODS FOR AUTOMATED IMAGE ANALYSIS FROM CARDIAC IMAGE DATA

(71) Applicants: Tufts Medical Center, Inc., Boston, MA (US); Gary M. Long, Boston, MA (US)

(72) Inventors: Benjamin S. Wessler, Boston, MA (US); Gary M. Long, Boston, MA (US)

(73) Assignees: Tufts Medical Center, Inc., Boston, MA (US); Gary Long, Boston, MA (US)

( * ) Notice: Subject to any disclaimer, the term of this patent is extended or adjusted under 35 U.S.C. 154(b) by 279 days.

(21) Appl. No.: 18/550,783

(22) PCT Filed: Mar. 17, 2022

(86) PCT No.: PCT/US2022/020797
§ 371 (c)(1),
(2) Date: Sep. 15, 2023

(87) PCT Pub. No.: WO2022/197955
PCT Pub. Date: Sep. 22, 2022

(65) Prior Publication Data

US 2024/0138817 A1 May 2, 2024

Related U.S. Application Data

(60) Provisional application No. 63/162,235, filed on Mar. 17, 2021.

(51) Int. Cl.

| | |
|---|---|
| ***A61B 8/00*** | (2006.01) |
| ***A61B 8/08*** | (2006.01) |
| *G06T 7/00* | (2017.01) |

(52) U.S. Cl.
CPC .......... *A61B 8/5223* (2013.01); *A61B 8/0883* (2013.01); *G06T 7/0012* (2013.01);
(Continued)

(58) Field of Classification Search
CPC ........... A61B 8/14; A61B 8/483; A61B 8/462; A61B 8/5223; A61B 8/0883; A61B 6/14;
(Continued)

(56) References Cited

U.S. PATENT DOCUMENTS

| | | | | |
|---|---|---|---|---|
| 2008/0249414 | A1 | 10/2008 | Yang et al. | |
| 2011/0262018 | A1 | 10/2011 | Kumar et al. | |
| 2021/0369243 | A1 * | 12/2021 | Zhou | G16H 40/67 |

FOREIGN PATENT DOCUMENTS

| | | | |
|---|---|---|---|
| WO | 2019178404 | A1 | 9/2019 |

OTHER PUBLICATIONS

Iung, Bernard, et al. “A prospective survey of patients with valvular heart disease in Europe: The Euro Heart Survey on Valvular Heart Disease.” European heart journal 24.13 (2003): 1231-1243.
(Continued)

*Primary Examiner* — Kent Yip
(74) *Attorney, Agent, or Firm* — Quarles & Brady LLP

(57) ABSTRACT

A system and method is provided for analyzing image data acquired from a patient. The method includes receiving image data associated with a patient, determining image frames with predetermined anatomical information from the cardiac image data, providing the image frames with the predetermined anatomical information to a trained model, and determining at least one of dimensional, volume, area, or physiological measurements using the trained model.

18 Claims, 14 Drawing Sheets

(52) U.S. Cl.
CPC .............. *G06T 2207/10132* (2013.01); *G06T 2207/20084* (2013.01)

(58) Field of Classification Search
CPC ......... A61B 6/541; A61B 6/462; A61B 6/503; G06T 7/0012; G06T 2207/10132; G06T 2207/20084
See application file for complete search history.

(56) References Cited

OTHER PUBLICATIONS

Bach, David S. "Prevalence and characteristics of unoperated patients with severe aortic stenosis." The Journal of heart valve disease 20.3 (2011): 284-291.
Benjamin, Emelia J., et al. "Heart disease and stroke statistics—2018 update: a report from the American Heart Association." Circulation 137.12 (2018): e67-e492.
Carpenter, Gail A., et al. "Fuzzy Artmap: A neural network architecture for incremental supervised learning of analog multidimensional maps." IEEE Transactions on neural networks 3.5 (1992): 698-713.
Long, Gary, and Benjamin S. Wessler. "Identification of Echocardiographic Imaging View Using Deep Learning." Circulation: Cardiovascular Quality and Outcomes 11.suppl_1 (2018): A276-A276.
Gulshan, Varun, et al. "Development and validation of a deep learning algorithm for detection of diabetic retinopathy in retinal fundus photographs." jama 316.22 (2016): 2402-2410.
Baumgartner, Helmut, et al. "Recommendations on the echocardiographic assessment of aortic valve stenosis: a focused update from the European Association of Cardiovascular Imaging and the American Society of Echocardiography." European Heart Journal—Cardiovascular Imaging 18.3 (2017): 254-275.
Pawełczyk, Krzysztof, et al. "Towards detecting high-uptake lesions from lung CT scans using deep learning." Image Analysis and Processing—ICIAP 2017: 19th International Conference, Catania, Italy, Sep. 11-15, 2017, Proceedings, Part II 19. Springer International Publishing, 2017.
Michelena, Hector I., et al. "Inconsistent echocardiographic grading of aortic stenosis: is the left ventricular outflow tract important ?." Heart 99.13 (2013): 921-931.
Montealegre-Gallegos, Mario, et al. "Cardiac output calculation and three-dimensional echocardiography." Journal of cardiothoracic and vascular anesthesia 28.3 (2014): 547-550.
Ronneberger, Olaf, Philipp Fischer, and Thomas Brox. "U-net: Convolutional networks for biomedical image segmentation." Medical Image Computing and Computer-Assisted Intervention—MICCAI 2015: 18th International Conference, Munich, Germany, Oct. 5-9, 2015, Proceedings, Part III 18. Springer International Publishing, 2015.
Russakovsky, Olga, et al. "Imagenet large scale visual recognition challenge." International journal of computer vision 115 (2015): 211-252.
Pibarot, Philippe, and Jean G. Dumesnil. "Low-flow, low-gradient aortic stenosis with normal and depressed left ventricular ejection fraction." Journal of the American College of Cardiology 60.19 (2012): 1845-1853.
Nishimura, Rick A., et al. "2014 AHA/ACC guideline for the management of patients with valvular heart disease: a report of the American College of Cardiology/American Heart Association Task Force on Practice Guidelines." Circulation 129.23 (2014): e521-e643.
International Search Report in PCT/US2022/020797; received on Jun. 14, 2022.

* cited by examiner

800

SYSTEMS AND METHODS FOR AUTOMATED IMAGE ANALYSIS FROM CARDIAC IMAGE DATA

CROSS-REFERENCE TO RELATED APPLICATIONS

This application is the national stage entry of PCT/US2022/020797, filed Mar. 17, 2022, which is based on, and claims priority to U.S. Provisional Application No. 63/162,235, filed Mar. 17, 2021. The contents of these applications are incorporated herein by reference.

STATEMENT REGARDING FEDERALLY SPONSORED RESEARCH

N/A.

BACKGROUND OF THE INVENTION

Medical imaging is a key tool in the practice of modern clinical medicine. Imaging is used in an extremely broad array of clinical situations, from diagnosis to delivery of therapeutics to guiding surgical procedures. While medical imaging provides an invaluable resource, it also consumes extensive resources. For example, imaging systems are expensive and are efficiently utilized when downtime is controlled. Furthermore, imaging systems require extensive human interaction to setup and operate, and then to analyze the images and make clinical decisions.

As just one example, cardiac ultrasound (i.e., echocardiography) is commonly used to image and diagnose patients with cardiac disease and/or cardiovascular disease. Cardiovascular disease (CVD) is responsible for about every one in three deaths in the United States. CVD is also responsible for approximately five hundred billion dollars of annual healthcare cost in the US.

Currently, echocardiograms are interpreted by a human clinician, such as a cardiologist, in order to diagnose patients. The clinician can use the echocardiograms to estimate the dimensions of certain areas of the heart, such as left ventricular outflow tract diameter (LVOTd) to calculate metrics that may indicate cardiac function, such as aortic valve area (AVA). AVA can indicate an estimated level of aortic stenosis. Additionally, echocardiograms are also used to quantify left ventricular function in order to estimate physiological parameters, such as ejection fraction and ventricular volumes in disease states, such as heart failure, hypertrophic cardiomyopathy, and valve disease.

Even with high-trained clinicians, the dimensions estimated by the clinician are prone to error because the clinician is required to manually mark dimensions on the cardiograms. Furthermore, the dimensions may be inconsistent from clinician to clinician, which can cause discontinuity between marked echocardiograms and potentially result in misdiagnosis of a patient. For example, an echocardiogram marked by one clinician may indicate that the patient does not have aortic stenosis, while the same echocardiogram marked by another clinician may indicate that the patient has moderate aortic stenosis. Ejection fraction also has high inter-reader variability due to both the selection of the correct end to the systolic and diastolic portions of the heart cycle and accurate tracings of the left ventricle.

Echocardiograms typically yield a large number of images, generally correspond to a large number of different views. In some cases, echocardiograms are organized with based on individual view, because only a portion of the views may be useful in calculating metrics, such as AVA. The large number of views and the comparatively small number of views needed for analysis can slow a practitioner in analyzing the echocardiogram data, as well as inflate the cost of cardiogram analysis.

Aggregated across various ultrasound applications, well beyond echocardiograms, and then aggregated across the multitude of imaging modalities (e.g., magnetic resonance imaging, computed tomography, positron emission tomography, optical imaging, digital pathology, and so on), reveals the need for extensive availability of high-trained human clinicians that operate in concert. It would therefore be desirable to provide systems and methods that reduce the overall need for human clinicians in medical imaging.

SUMMARY OF THE INVENTION

The present disclosure provides systems and methods that reduce the total investment of human time required for medical imaging applications. In one non-limiting example, systems and methods are provided for automatically analyzing images, for example, such as echocardiograms.

In accordance with one aspect of the disclosure, a cardiac image analysis system is provided that includes at least one processor and at least one memory. The cardiac image analysis system is configured to receive cardiac image data associated with the patient, determine apical chamber image frames included in the cardiac image data, provide the apical chamber image frames to a trained model, receive tracing coordinates from the trained model, and receive grid cell classifications from the trained model. The system is further configured to determine a change in left ventricular volume for apical chambers of the patient based on the tracing coordinates and the grid cell classifications and determine ejection fraction for the patient based on the change in left ventricular volume for the apical chambers of the patient.

In accordance with another aspect of the disclosure, a cardiac image analysis method is provided that includes receiving cardiac image data associated with a patient, determining apical chamber image frames included in the cardiac image data, providing the apical chamber image frames to a trained model, and receiving tracing coordinates from the trained model. The method also includes receiving grid cell classifications from the trained model, determining a change in left ventricular volume for apical chambers of the patient based on the tracing coordinates and the grid cell classifications, and determining ejection fraction for the patient based on the change in left ventricular volume for the apical chambers of the patient.

The foregoing and other aspects and advantages of the invention will appear from the following description. In the description, reference is made to the accompanying drawings which form a part hereof, and in which there is shown by way of illustration embodiments of the invention. Any such embodiment does not necessarily represent the full scope of the invention, however, and reference is made therefore to the claims and herein for interpreting the scope of the invention.

DETAILED DESCRIPTION OF THE INVENTION

The present disclosure provides systems and methods that can reduce human and/or trained clinician time required to analyze medical images. As one non-limiting example, the present disclosure provides example of the inventive concepts provided herein applied to the analysis of echocardiograms, however, other imaging modalities beyond ultrasound and applications within each modality are contemplated, such as MRI, CT, PET, SPECT, optical, digital pathological images, and the like.

In the non-limiting example of echocardiograms, the systems and methods provided herein can determine metrics such as ejection fraction, apical and ventricular volumes and dimensions, wall thickness, motion parameters, left ventricular outflow tract diameter (LVOTd), aortic valve velocity time integral (VTI), left ventricular outflow tract (LVOT) VTI, and/or aortic valve area (AVA) for a patient based on cardiac imaging data such as echocardiogram data. The systems and methods provided herein can also determine maximum aortic valve pressure gradient and/or mean aortic valve pressure gradient for the patient without any human input. The systems and methods can provide consistent estimates for various cardiac metrics across different patients, practitioners, hospitals, and the like.

Figure 1:
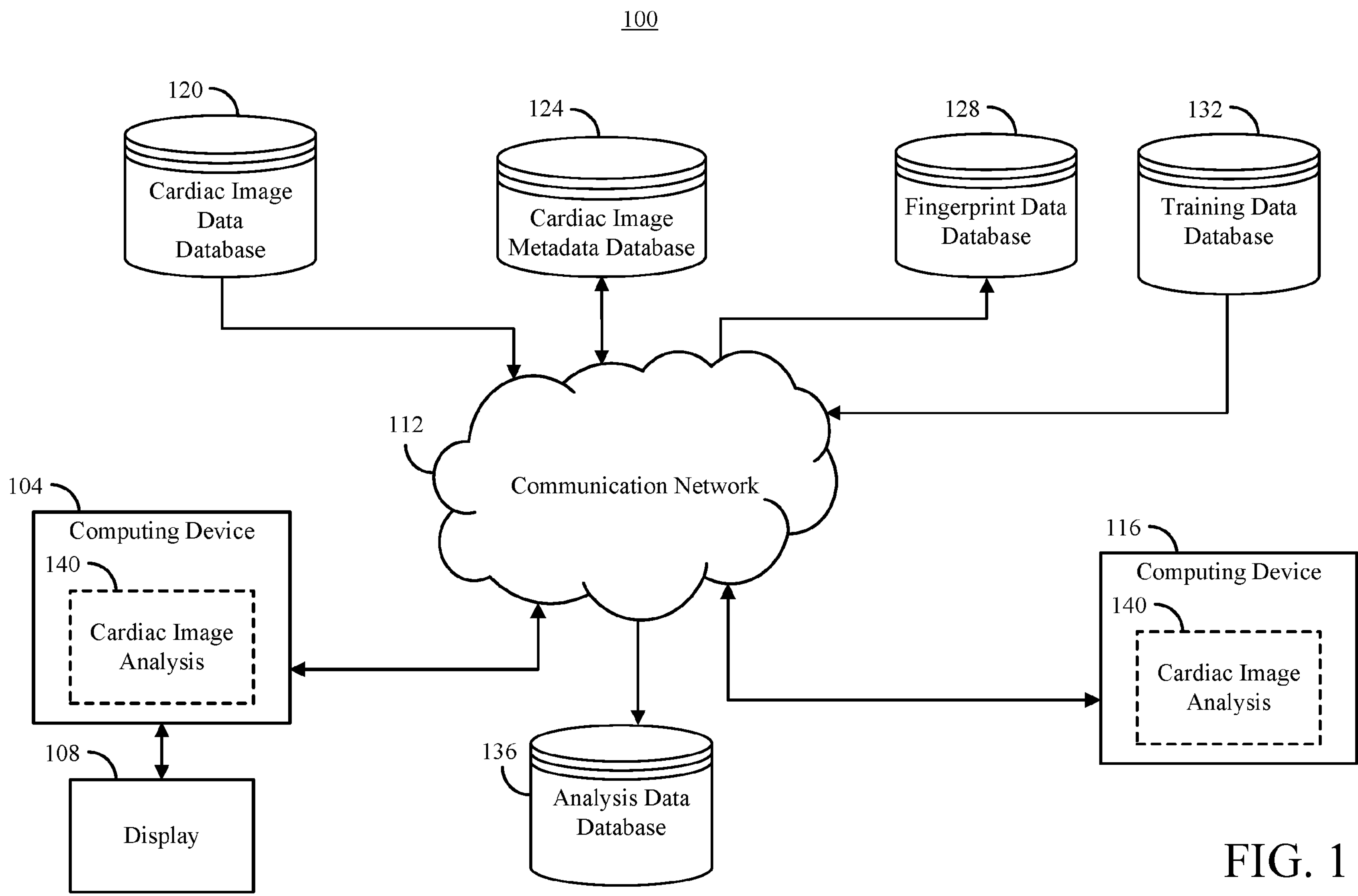
FIG. 1 is an example of a cardiac image analysis system in accordance with the disclosed subject matter.

FIG. 1 shows an example of a cardiac image analysis system 100 in accordance with some aspects of the disclosed subject matter. In some configurations, the cardiac image analysis system 100 can include a computing device 104, a display 108, a communication network 112, a supplemental computing device 116, a cardiac image data database 120, a cardiac image metadata database 124, a fingerprint data database 128, a training data database 132, and an analysis data database 136. The computing device 104 can be in communication (e.g., wired communication, wireless communication) with the display 108, the supplemental computing device 116, the cardiac image data database 120, the cardiac image metadata database 124, the fingerprint data database 128, the training data database 132, and the analysis data database 136.

The computing device 104 can implement portions of a cardiac image analysis application 140, which can involve the computing device 104 transmitting and/or receiving instructions, data, commands, etc. from one or more other devices. For example, the computing device 104 can receive cardiac image data from the cardiac image database 120, receive training data from the training data database 132, receive and transmit cardiac image metadata from the cardiac image metadata database 124, transmit fingerprint data generated by the cardiac image analysis application 140 to the fingerprint data database 128, and transmit reports and/or raw data generated by the cardiac image analysis application 140 to the display 108 and/or the analysis data database 136.

The supplementary computing device 116 can implement portions of the cardiac image analysis application 140. It is understood that the cardiac image analysis system 100 can implement the cardiac image analysis application 140 without the supplemental computing device 140. In some aspects, the computing device 104 can cause the supplemental computing device 116 to receive cardiac image data from the cardiac image database 120, receive training data from the training data database 132, receive and transmit cardiac image metadata from the cardiac image metadata database 124, transmit fingerprint data generated by the cardiac image analysis application 140 to the fingerprint data database 128, and transmit reports and/or raw data generated by the cardiac image analysis application 140 to the display 108 and/or the analysis data database 136. In this way, a majority of the cardiac image analysis application 140 can be implemented by the supplementary computing device 116, which can allow a larger range of device to be used as the computing device 104 because the required processing power of the computing device 104 may be reduced.

The cardiac image data database 120 can include cardiac image data, such as echocardiogram data. The echocardiogram data may be formatted in the DICOM® standard (i.e., format). The echocardiogram data can include one or more DICOM® objects associated with a patient. Each DICOM® object can include image data (e.g., pixel data) formatted in various standards such as JPEG, lossless JPEG, JPEG 2000, etc. Each DICOM® object can also include attributes about the patient and/or the image data (e.g., a view associated with the image data).

The cardiac image metadata database 124 can include metadata extracted from cardiac image data. The cardiac image analysis application 140 can generate the metadata can be generated based on echocardiogram data received from the cardiac image data database 120. The metadata can be associated with a DICOM® object. The metadata can include parameters such as patient age binned into age ranges following HIPAA rules, BMI, heart rate, image size, number of image frames (e.g., the number of image frames in the image data), units in the image frames (e.g., the scale of each image frame), whether or not the data contains Doppler tracings (e.g., true or false), whether or not the image was a thumbnail view, the location of the image frames within the sequence of images taken during the study (e.g., the image frames were the sixth and seventh images generated, respectively), image scaling data, and other data suitable for analyzing cardiac image data.

The fingerprint data database 128 can include "fingerprint" data associated with cardiac image data. The cardiac image analysis application 140 can generate fingerprint data based on echocardiogram data received from the cardiac image data database 120. In some configurations, the cardiac image analysis application 140 can provide at least a portion of a DICOM® object to a trained convolutional neural network (CNN). The cardiac image analysis application 140 can provide a portion of the DICOM®or other formatted file corresponding to image data without patient information overlay and other relevant metadata contained in the DICOM header to the trained CNN. In some configurations, the trained CNN can include a VGG 16 network, an Inception V1 network, and/or an Inception V3 network. In some configurations, the CNN can be trained using transfer learning to move weights for one or more CNNs pre-trained using ImageNet data, and then training the CNNs using echocardiogram training data. The trained CNN can output a vector of floating point numbers. The cardiac image analysis application 140 can receive the vector of floating point numbers, convert the vector to a string, compress the string, and output the string to the fingerprint data database 128. The string can be provided to another machine learning model, such as a CNN, and used to refine classification of image data. The string can assist in retraining downstream layers by providing a stored "fingerprint" of image data. Using 3D temporal convolutional networks, multiple frames can be incorporated into a single fingerprint that encodes the spatiotemporal nature of the data.

The training data database 132 can include training data that the cardiac image analysis application 140 can use to train one or more machine learning models including neural networks such as CNNs. More specifically, the training data can include annotated training images (e.g., human annotated training images) that can be used to train one or more machine learning models using a supervised learning process. The training data will be discussed in further detail below.

The cardiac image analysis application 140 can automatically generate one or more cardiac metrics such as ejection fraction, apical and ventricular volumes and dimensions, wall thickness, motion parameters, LVOTd, aortic valve VTI, LVOT VTI, AVA, maximum aortic valve pressure gradient, and/or mean aortic valve pressure gradient for a patient based on cardiac imaging data such as echocardiogram data. The cardiac image analysis application 140 can also automatically generate one or more reports based on the ejection fraction, the apical and ventricular volumes and dimensions, the wall thickness, the motion parameters, the LVOTd, aortic valve VTI, LVOT VTI, AVA, maximum aortic valve pressure gradient, and/or mean aortic valve pressure gradient (and by extension, the cardiac image data). The cardiac image analysis application 140 can output one or more of the cardiac metrics and/or reports to the display 108 (e.g., in order to display the cardiac metric and/or reports to a medical practitioner) and/or to a memory, such as a memory included in the analysis data database 136 (e.g., in order to store the cardiac metric and/or reports).

As shown in FIG. 1, the communication network 112 can facilitate communication between the computing device 104, the supplemental computing device 116, the cardiac image data database 120, the cardiac image metadata database 124, the fingerprint data database 128, the training data database 132, and the analysis data database 136. In some configurations, communication network 112 can be any suitable communication network or combination of communication networks. For example, communication network 112 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some configurations, communication network 112 can be a local area network, a wide area network, a public network (e.g., the Internet), a private or semi-private network (e.g., a corporate or university intranet), any other suitable type of network, or any suitable combination of networks. Communications links shown in FIG. 1 can each be any suitable communications link or combination of communications links, such as wired links, fiber optic links, Wi-Fi links, Bluetooth links, cellular links, and the like.

Figure 2:
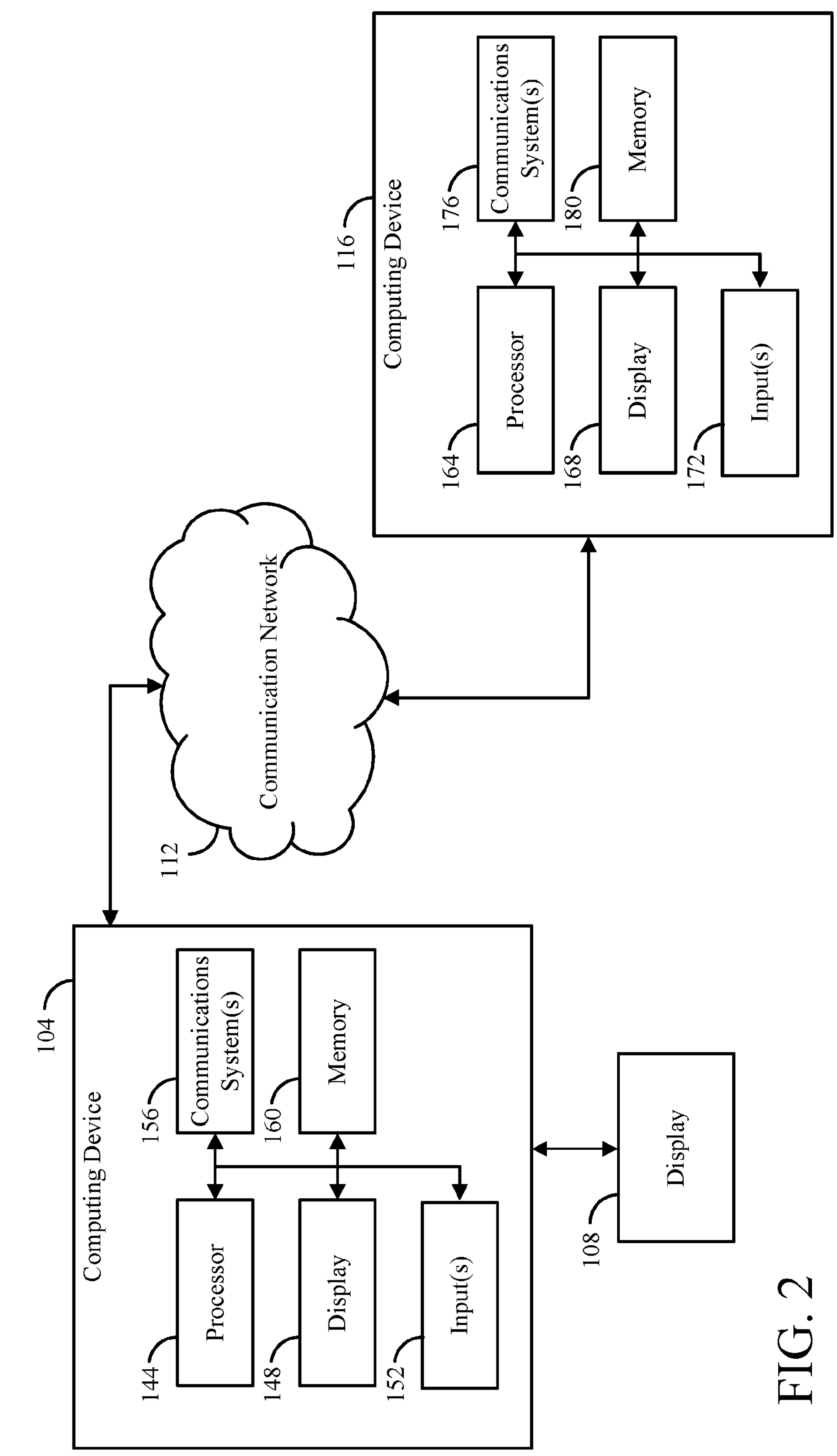
FIG. 2 is an example of hardware that can be used to implement a computing device and a supplemental computing device shown in FIG. 1 in accordance with the disclosed subject matter.

FIG. 2 shows an example of hardware that can be used to implement a computing device 104 and a supplemental computing device 116 shown in FIG. 1 in accordance with some aspects of the disclosed subject matter. As shown in FIG. 2, the computing device 104 can include a processor 144, a display 148, an input 152, a communication system 156, and a memory 160. The processor 144 can implement at least a portion of the cardiac image analysis application 140, which can, for example, be executed from a program (e.g., saved and retrieved from the memory 160). The processor 144 can be any suitable hardware processor or combination of processors, such as a central processing unit ("CPU"), a graphics processing unit ("GPU"), etc., which can execute a program, which can include the processes described below.

In some configurations, the display 148 can present a graphical user interface. In some configurations, the display 148 can be implemented using any suitable display devices, such as a computer monitor, a touchscreen, a television, etc. In some configurations, the inputs 152 of the computing device 104 can include indicators, sensors, actuatable buttons, a keyboard, a mouse, a graphical user interface, a touch-screen display, etc. In some configurations, the inputs 152 can allow a user (e.g., a medical practitioner, such as a cardiologist) to interact with the computing device 104, and thereby to interact with the supplemental computing device 116 (e.g., via the communication network 112). The display 108 can be a display device such as a computer monitor, a touchscreen, a television, and the like.

In some configurations, the communication system 156 can include any suitable hardware, firmware, and/or software for communicating with the other systems, over any suitable communication networks. For example, the communication system 156 can include one or more transceivers, one or more communication chips and/or chip sets, etc. In a more particular example, the communication system 156 can include hardware, firmware, and/or software that can be used to establish a coaxial connection, a fiber optic connection, an Ethernet connection, a USB connection, a Wi-Fi connection, a Bluetooth connection, a cellular connection, etc. In some configurations, the communication system 156 allows the computing device 104 to communicate with the supplemental computing device 116 (e.g., directly, or indirectly such as via the communication network 112).

In some configurations, the memory 160 can include any suitable storage device or devices that can be used to store instructions, values, etc., that can be used, for example, by the processor 144 to present content using the display 148 and/or the display 108, to communicate with the supplemental computing device 116 via communications system(s) 156, etc. The memory 160 can include any suitable volatile memory, non-volatile memory, storage, or any suitable combination thereof. For example, the memory 160 can include RAM, ROM, EEPROM, one or more flash drives, one or more hard disks, one or more solid state drives, one or more optical drives, etc. In some configurations, the memory 160 can have encoded thereon a computer program for controlling operation of the computing device 104 (or the supplemental computing device 116). In such configurations, the processor 144 can execute at least a portion of the computer program to present content (e.g., user interfaces, images, graphics, tables, reports, and the like), receive content from the supplemental computing device 116, transmit information to the supplemental computing device 116, and the like.

Still referring to FIG. 2, the supplemental computing device 116 can include a processor 164, a display 168, an input 172, a communication system 176, and a memory 180. The processor 164 can implement at least a portion of the cardiac image analysis application 140, which can, for example, be executed from a program (e.g., saved and retrieved from the memory 180). The processor 164 can be any suitable hardware processor or combination of processors, such as a central processing unit ("CPU"), a graphics processing unit ("GPU"), and the like, which can execute a program, which can include the processes described below.

In some configurations, the display 168 can present a graphical user interface. In some configurations, the display 168 can be implemented using any suitable display devices, such as a computer monitor, a touchscreen, a television, etc. In some configurations, the inputs 172 of the supplemental computing device 116 can include indicators, sensors, actuatable buttons, a keyboard, a mouse, a graphical user interface, a touch-screen display, etc. In some configurations, the inputs 172 can allow a user (e.g., a medical practitioner, such as a cardiologist) to interact with the supplemental computing device 116, and thereby to interact with the computing device 104 (e.g., via the communication network 112).

In some configurations, the communication system 176 can include any suitable hardware, firmware, and/or software for communicating with the other systems, over any suitable communication networks. For example, the communication system 176 can include one or more transceivers, one or more communication chips and/or chip sets, etc. In a more particular example, the communication system 176 can include hardware, firmware, and/or software that can be used to establish a coaxial connection, a fiber optic connection, an Ethernet connection, a USB connection, a Wi-Fi connection, a Bluetooth connection, a cellular connection, and the like. In some configurations, the communication system 176 allows the supplemental computing device 116 to communicate with the computing device 104 (e.g., directly, or indirectly such as via the communication network 112).

In some configurations, the memory 180 can include any suitable storage device or devices that can be used to store instructions, values, and the like, that can be used, for example, by the processor 164 to present content using the display 168 and/or the display 108, to communicate with the computing device 104 via communications system(s) 176, and the like. The memory 180 can include any suitable volatile memory, non-volatile memory, storage, or any suitable combination thereof. For example, the memory 180 can include RAM, ROM, EEPROM, one or more flash drives, one or more hard disks, one or more solid state drives, one or more optical drives, etc. In some configurations, the memory 180 can have encoded thereon a computer program for controlling operation of the supplemental computing device 116 (or the computing device 104). In such configurations, the processor 164 can execute at least a portion of the computer program to present content (e.g., user interfaces, images, graphics, tables, reports, and the like), receive content from the computing device 104, transmit information to the computing device 104, and the like.

Figure 3:
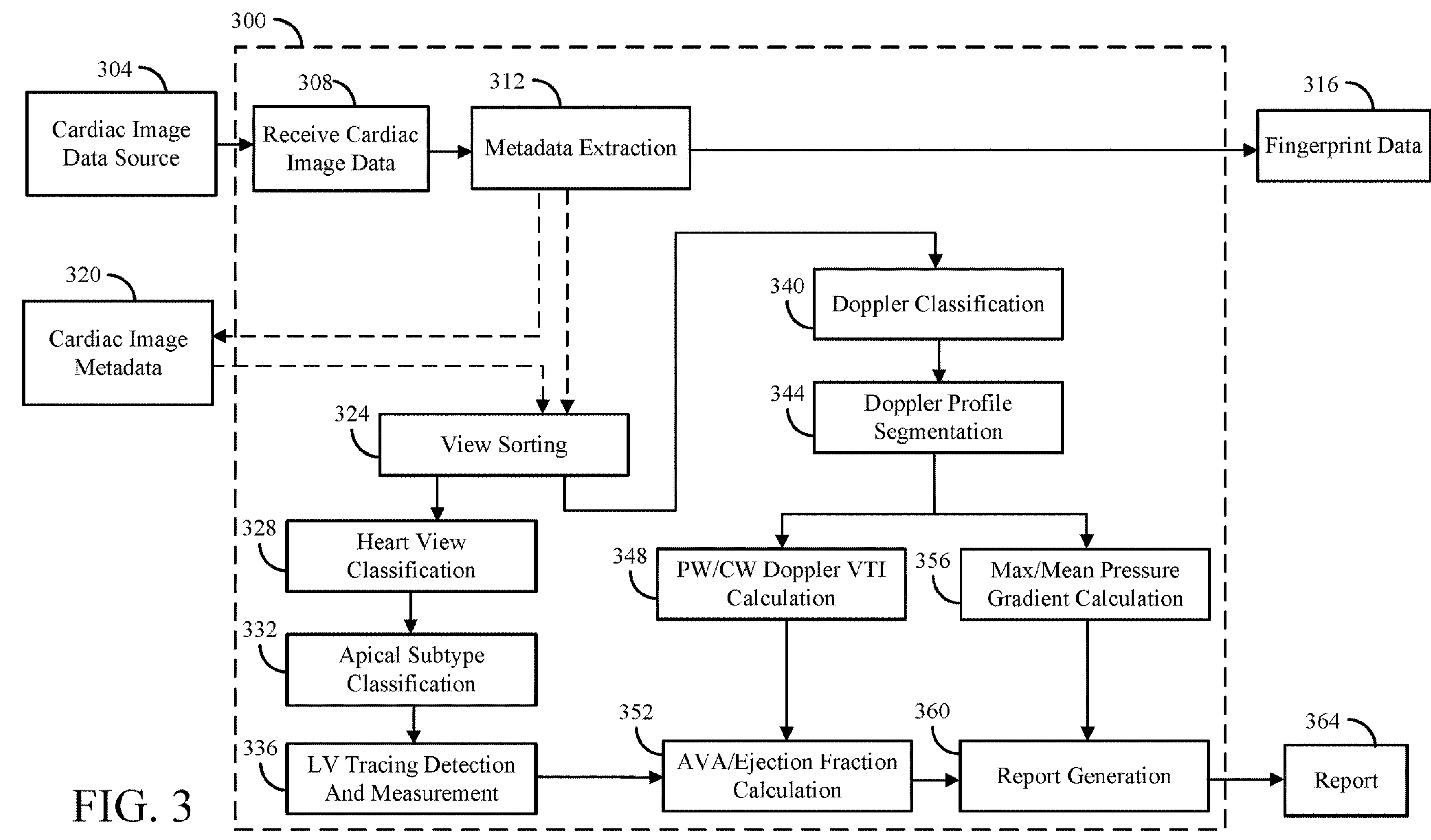
FIG. 3 is a schematic illustration of a cardiac image analysis flow in accordance with the disclosed subject matter.

Referring now to FIG. 1 as well as FIG. 3, a schematic illustration of a cardiac image analysis flow 300 in accordance with some aspects of the disclosed subject matter is shown. The cardiac image analysis flow 300 can be used to implement at least a portion of the cardiac image analysis application 140. Thus, the cardiac image analysis flow 300 can be implemented using the cardiac image analysis system 100. The flow 300 can include a number of processes for sorting data, extracting data, and otherwise processing data, as well as include providing data to and receiving data from a number of trained machine learning models such as neural networks. Exemplary processes and machine learning models will be described in detail below.

The cardiac image analysis flow 300 begins at and includes receiving cardiac image data 308. The cardiac image analysis flow 300 can receive cardiac image data from a cardiac image data source 304. The cardiac image data source 304 can include the cardiac image database 120. The cardiac image data can include a number of imaging objects. Each imaging object can include one or more image frames of image data (e.g., digital pictures), as well as a number of attributes. The cardiac image data can include echocardiogram data that may be formatted in the DICOM® standard or image format.

The echocardiogram data can include a number of imaging objects that each include a number of attributes and a number of image frames (e.g., individual images). After receiving cardiac image data 308, the cardiac image analysis flow 300 can include extracting metadata 312 from the cardiac image data.

The extracting metadata 312 can include generating fingerprint data based on the cardiac image data. In some configurations, the extracting metadata 312 can include providing at least a portion of a DICOM® object to a trained CNN, receiving a vector of floating point numbers from the trained CNN, converting the vector to a string, compressing the string, and outputting the string as fingerprint data 316. The portion of the DICOM® object can include image frames (e.g., JPEG images) that have any personal patient health information redacted. The portion of the DICOM® object can also include patient attributes such as age, heart rate, sex, etc. In some configurations, the trained CNN can include a number of feed-forward convolution blocks, pooling layers, and non-linear activation functions, and may include skip connections. In some configurations, the trained single frame DICOMS CNN can include an inflated 3D CNN such as an Inception 3D network (I3D) that receives multiple temporal frames for the DICOM region. For DICOM® objects with a single image frame, a 3D CNN can produce the same output as a 2D CNN.

The fingerprint data 316 can be output to a memory or other suitable storage medium that may be included in the fingerprint data database 128. The flow 300 can include extracting data for any number of imaging objects associated with a patient and/or a study associated with a patient. For example, the imaging objects can be associated with an echocardiogram study (e.g., a transthoracic echocardiogram study) performed for a patient. The echocardiogram study may have generated on or more image frames for multiple different views of the patient's heart. In some configurations, the imaging objects can include at least a portion of a transthoracic echocardiogram image dataset associated with the patient.

The extracting metadata 312 can include extracting metadata from the imaging objects. The metadata can include parameters such as patient age binned into age ranges following HIPAA rules, BMI, heart rate, image size, number of image frames (e.g., the number of image frames in the image data), units in the image frames (e.g., the scale of each image frame), whether or not the data (e.g., the imaging object) contains Doppler tracings (e.g., true or false), whether or not the image was a thumbnail view, the location of the image frames within the sequence of images taken during the study (e.g., the image frames were the sixth and seventh images generated, respectively), image scaling data, and other data suitable for analyzing cardiac image data. The metadata can be extracted from attributes (i.e., fields) included in the imaging objects. The flow 300 may output the metadata to a cardiac image metadata database 320.

The flow 300 can include view sorting 324 the imaging objects included in the cardiac image data. The view sorting 324 can include identifying which imaging objects and/or image frames included in the objects include Doppler tracings based on the metadata. As mentioned above, each imaging object can include an attribute that indicates whether or not the data contains Doppler tracings (e.g., true or false). The flow 300 can include performing Doppler classification 340 for views that contain Doppler tracings (i.e., Doppler views, which is described further below. The flow 300 can include performing heart view classification 328 for views that do not contain Doppler tracings (i.e., non-Doppler views).

The heart view classification 328 can include providing each of the non-Doppler views to a trained classifier, and receiving an indication of whether or not each non-Doppler view is an apical view, such as an apical 4 chamber view, an apical 2 chamber view, or the like. As one example, in some configurations, the heart view classification 328 may receive an indication of whether or note that each non-Doppler view is a parasternal long axis (PLAX) view. In some configurations, the trained classifier can include a trained convolutional neural network (CNN), such as a Google Inception V3 network. In some configurations, the trained classifier can include a 3D CNN such as an Inception 3D network. In some configurations, the heart view classification 328 can include identifying which of the non-Doppler views is an apical view using the metadata associated with each view. For example, the metadata may include an attribute that indicates if the view is an apical view or not (e.g., true or false). However, the trained classifier can be particularly in processing non-annotated, under-annotated, or incorrectly annotated views, and thus may reduce the amount of human effort involved in analyzing echocardiogram data.

The heart view classification 328 can also include identifying each apical view as a non-zoomed apical view or a zoomed apical view based on the metadata. The heart view classification 328 can determine that imaging objects identified to be an apical view that only include a single image frame of imaging data and no thumbnail are zoomed apical views. The heart view classification 328 can determine all other apical views are non-zoomed apical views.

The heart view classification 328 can also include determining a calcification amount for each apical view (zoomed and non-zoomed). In some configurations, the heart view classification 328 can include providing each of the non-zoomed apical views to a trained classifier such as a CNN in order to type each non-zoomed apical view as normally calcified, mildly calcified, moderately calcified, or severely calcified. In some configurations, the CNN can be pre-trained on ImageNet and tuned without modifying weights on echocardiogram data in order to provide a common front end to downstream classifiers and/or models. The heart view classification 328 may also include providing each of the zoomed apical views to a trained classifier in order to type each zoomed apical view as normally calcified, mildly calcified, moderately calcified, or severely calcified. If one or more of the apical views are mildly calcified, moderately calcified, or severely calcified, the flow 300 can pass to apical subtype classification 332.

After the heart view classification 328, the flow can include apical subtype classification 332. The apical subtype classification 332 can include providing the apical views identified at the heart view classification 328 to a trained classifier such as a CNN, and receiving a quality metric for each view. The quality metric may indicate a level of confidence that the view is a suitable view of, e.g., the ejection fraction, the LVOTd, and the like. After generating the quality metric, the flow 300 can pass to LV tracing detection and measurement 336.

After the apical subtype classification 332, the flow can include LV tracing detection and measurement 336. In some configurations, the LV tracing detection and measurement 336 can include providing apical views associated with a quality metric above a predetermined threshold to a trained machine learning model. The trained machine learning model can include a CNN trained to identify endpoints of the diameter of the LV tracing in the apical views. An example of such a model is described below in conjunction with FIGS. 4, 5, and 6. Once the endpoints of the LV tracing are identified in each view, the LV tracing detection and measurement 336 can include calculating, e.g, the left ventricular volumes, the ejection fraction, the LVOTd, or the like for each view using image scaling data. The LV tracing detection and measurement 336 may then average or track the calculated left ventricular volumes, LVOTds, or the like across all apical views to determine end systolic and end diastolic volumes, a final LVOTd, or the like. A LV tracing is converted into a volume using the monoplane Simpson calculation (summation of disks) by creating slices of the tracing conforming to stacked cylindrical sample volumes with a diameter equal to the orthogonal vector joining the left and right sides of the tracing that passes through uniformly spaced points along the longitudinal axis joining the LV apex and the midpoint between the Mitral Valve anchor points. When Apical 2 and 4 views are identified (via the apical subtype classification 332), the biplane Simpson calculation can be used where lengths of sample volumes from matching end systolic or end diastolic frames can be used to define orthogonal vectors forming the axes of a stack of ellipsoid volumes. When available, the biplane Simpson method is used as a method for ejection fraction calculation following clinical practice. The final ejection fraction is computed from a difference between the end diastolic and the end systolic volumes divided by the end diastolic volume. The final LVOTd and the VTIs are used to calculate AVA for a patient.

The flow 300 can include Doppler classification 340. After Doppler views are identified, the Doppler classification 340 can provide the Doppler views to a trained classifier that can output a view indication for each view. In some configurations, to determine if a Doppler view is of the aortic valve, the flow 300 can include providing a Doppler image frame to a CNN, receiving an output for the Doppler image frame, providing a thumbnail image associated with the Doppler image to the CNN, receiving an output associated with the thumbnail image, and providing the outputs associated with the thumbnail image and the Doppler image frame to the classifier. The Doppler classification 340 can include identifying which Doppler views are views of the aortic valve. The Doppler classification 340 can also determine which Doppler views are continuous-wave (CW) Doppler profiles, as well as which Doppler views are pulsed-wave (PW) Doppler profiles. The CW and PW Doppler profiles can be determined based on metadata associated with each Doppler view (e.g., metadata extracted from the imaging object associated with the view), and the Doppler profiles can be classified as aortic valve views using a trained classifier as described above. Each Doppler view of the aortic valve can be analyzed at Doppler profile segmentation 344.

The flow 300 can include Doppler profile segmentation 344. The Doppler profile segmentation 344 can include generating annotations indicating the outline of the Doppler profile, and more specifically, the VTI interval. In some aspects, the Doppler profile segmentation 344 can include providing the PW Doppler profiles of the aortic valve to a trained machine learning model. The trained machine learning model can be a CNN trained to trace a VTI envelope for each image frame included in a PW Doppler view of the aortic valve. An example of this CNN is described further below. The CNN can mark pixels that are included in the VTI envelope.

In some configurations, the Doppler profile segmentation 344 can include providing the CW Doppler profiles of the aortic valve to a trained machine learning model. The trained machine learning model can be a CNN trained to trace a VTI envelope for each image frame included in a CW Doppler view of the aortic valve. An example of this CNN is described further below. The CNN can mark pixels that are included in the VTI envelope.

The flow 300 can include PW/CW Doppler VTI calculation 348. The PW/CW Doppler VTI calculation 348 can include determining VTI over the PW Doppler profiles (i.e., PW VTI) and the VTI over the CW Doppler profiles (i.e., CW VTI). The PW VTI and the CW VTI, along with the LVOTd determined at the LVOTd detection and measurement 336, can be used to determine aortic valve area for the patient. In some configurations, the PW/CW Doppler VTI calculation 348 can include determining PW VTI based on the marked pixels indicating the VTI envelope generated for the PW Doppler profiles at the Doppler profile segmentation 344. In some configurations, the PW/CW Doppler VTI calculation 348 can include determining CW VTI based on the marked pixels indicating the VTI envelope generated for the CW Doppler profiles at the Doppler profile segmentation 344.

The PW/CW Doppler VTI calculation 348 can include determining and removing outliers in the marked pixels for the PW Doppler profiles. If the marked pixels of one image frame are not similar enough to an average of the marked pixels of other image frames, the PW/CW Doppler VTI calculation 348 can remove the image frame and the marked pixels associated from the image frame. The PW/CW Doppler VTI calculation 348 can determine the outliers by comparing the location of each marked pixel for a given image frame to the average location of the corresponding marked pixel in the other image frames. If the marked pixels of the image frame differ from the average marked pixels in other image frames by a predetermined threshold (e.g., by five pixels), the PW/CW Doppler VTI calculation 348 can determine the marked pixels of the image frame are outliers and should be removed. In some configurations, multiple VTI profiles can be drawn per Doppler view because multiple heartbeats (e.g., 3 heartbeats) are recorded. To determine outliers, the flow 300 can only combine Doppler image frames marked pixels that in total (e.g., as an envelope), are within a predetermined percent difference of the marked pixels of the other Doppler image frames.

In some configurations, the PW/CW Doppler VTI calculation 348 can include determining the Doppler envelope segmentation using a morphological operation, such as generating a filled mask from a set of pixels that are above a background threshold. In some configurations, the flow 300 can include providing Doppler profiles to a segmentation network such as a U-Net to perform VTI segmentation, and using morphological operations to cluster pixel coming out of that network. The morphological operation can determine the Doppler envelope segmentation based on the marked pixels. The PW/CW Doppler VTI calculation 348 can determine the PW VTI based on the Doppler envelope segmentation and scaling information associated with the image frame(s) (e.g., one pixel is one millimeter in length), and may average the PW VTI obtained for each image frame and/or PW Doppler view. The averaged PW VTI can be used as a final PW VTI used in the AVA equation. However, it is appreciated that the final PW VTI can be the raw PW VTI determined for a single image frame.

The PW/CW Doppler VTI calculation 348 can include determining and removing outliers in the marked pixels for the CW Doppler profiles. If the marked pixels of one image frame are not similar enough to an average of the marked pixels of other image frames, the PW/CW Doppler VTI calculation 348 can remove the image frame and the marked pixels associated from the image frame. The PW/CW Doppler VTI calculation 348 can determine the outliers by comparing the location of each marked pixel for a given image frame to the average location of the corresponding marked pixel in the other image frames. If the marked pixels of the image frame differ from the average marked pixels in other image frames by a predetermined threshold (e.g., by five pixels), the PW/CW Doppler VTI calculation 348 can determine the marked pixels of the image frame are outliers and should be removed. In some configurations, multiple VTI profiles can be drawn per Doppler view because multiple heartbeats (e.g., 3 heartbeats) are recorded. To determine outliers, the flow 300 can only combine Doppler image frames marked pixels that in total (e.g., as an envelope), are within a predetermined percent difference of the marked pixels of the other Doppler image frames.

In some configurations, the PW/CW Doppler VTI calculation 348 can include determining the Doppler envelope segmentation using a morphological operation, such as morphological dilation and erosion using a structural element or binary clustering using connected components. The morphological operation can determine the Doppler envelope segmentation based on the marked pixels. The PW/CW Doppler VTI calculation 348 can determine the CW VTI based on the Doppler envelope segmentation and scaling information associated with the image frame(s) (e.g., one pixel is one millimeter in length), and may average the CW VTI obtained for each image frame and/or CW Doppler view. The averaged CW VTI can be used as a final CW VTI used in the AVA equation. However, it is appreciated that the final CW VTI can be the raw CW VTI determined for a single image frame.

The flow 300 can include an AVA/ejection fraction calculation 352 (also referred to herein as "the calculation block 352"). The calculation block 352 may include an ejection fraction calculation when apical views are processed or an aortic valve area (AVA) calculation when PLAX views are processed. After the PW VTI and the CW VTI have been calculated (e.g., at the PW/CW Doppler VTI calculation 348) or the LV tracing has been calculated (e.g., at the LV tracing detection and measurement 336), the flow 300 can pass the calculation 352 (e.g., for the ejection fraction calculation). The calculation block 352 can include calculating AVA according to the following equation:

$$AVA = \frac{\pi\left(\frac{LVOTd}{2}\right)^2 VTI_1}{VTI_2}; \tag{1}$$

where $VTI_1$ is the PW VTI and $VTI_2$ is the CW VTI.

The ejection fraction calculation can be included here when processing apical views. Minimum and maximum LV volumes define the end systolic and end diastolic volumes respectfully. The following calculation is used to compute the ejection fraction:

Ejection Fraction=100×(EDV−ESV)/EDV where EDV is the end diastolic volume and ESV is the end systolic volume.

The flow 300 can include peak and mean pressure gradient calculation 356. In some configurations, the peak and mean pressure gradient calculation 356 can determine PW VTI and CW VTI in substantially similar fashion as described above in conjunction with the PW/CW Doppler VTI calculation 348. After the PW VTI and CW VTI are calculated, the peak and mean pressure gradient calculation 356 can determine the maximum pressure gradient and the mean pressure gradient.

To determine the maximum pressure gradient, the peak and mean pressure gradient calculation 356 can include determining peak locations of VTI for the PW Doppler views and/or the CW Doppler views, converting the peak locations of VTI into units of mmHg based on metadata associated with the view (e.g., x and y units included in the metadata), and outputting the maximum pressure gradient (having units of mmHg) for the PW Doppler views and/or the CW Doppler views. Thus, the peak and mean pressure gradient calculation 356 may calculate the CW maximum pressure gradient and/or the PW maximum pressure gradient.

To determine the mean pressure gradient, the peak and mean pressure gradient calculation 356 can include determining VTI for each the PW Doppler views and/or the CW Doppler views, converting the VTI into units of mmHg based on metadata associated with the view, and averaging VTI in units of mmHg (i.e., the maximum pressure gradient). Thus, the peak and mean pressure gradient calculation 356 may calculate the CW mean pressure gradient and/or the PW mean pressure gradient.

The flow 300 can include report generation 360. After the ejection fraction, the maximum pressure gradient, and/or the mean pressure gradient are calculated, the flow 300 can generate a report based on the ejection fraction, the maximum pressure gradient, and/or the mean pressure gradient. The report generation 360 can also generate the report based on the ejection fraction, the AVA, the PW VTI, the CW VTI, the mean pressure gradient, the maximum pressure gradient, the LVOTd, any of the information included in the metadata extracted at the metadata extraction 312, the classifications and/or scores generated at the heart view classification 328, the Apical subtype classification, and/or the Doppler classification, annotations such as the marked pixels determined at the Doppler profile segmentation 344 and/or the endpoints determined at the LV tracing detection and measurement 336, or other suitable information determined or received by the flow 300. The report can visual representations of the annotations (e.g., the annotations overlaid on an image frame). The report can include a classification indicating the severity of the ejection fraction. The flow 300 can include outputting the report 364.

It is appreciated that the flow 300 can include outputting any of the metrics, segmentations, classified views, metadata, etc. calculated or otherwise determined by modules included in the flow 300. For example, the flow 300 may include outputting the ejection fraction, the AVA, the PW VTI, the CW VTI, the mean pressure gradient, the maximum pressure gradient, the LVOTd, any of the information included in the metadata extracted at the metadata extraction 312, the classifications and/or scores generated at the heart view classification 328, the apical subtype classification, and/or the Doppler classification, annotations such as the marked pixels determined at the Doppler profile segmentation 344 and/or the endpoints determined at the LV tracing detection and measurement 336, or other suitable information determined or received by the flow 300.

Figure 4:
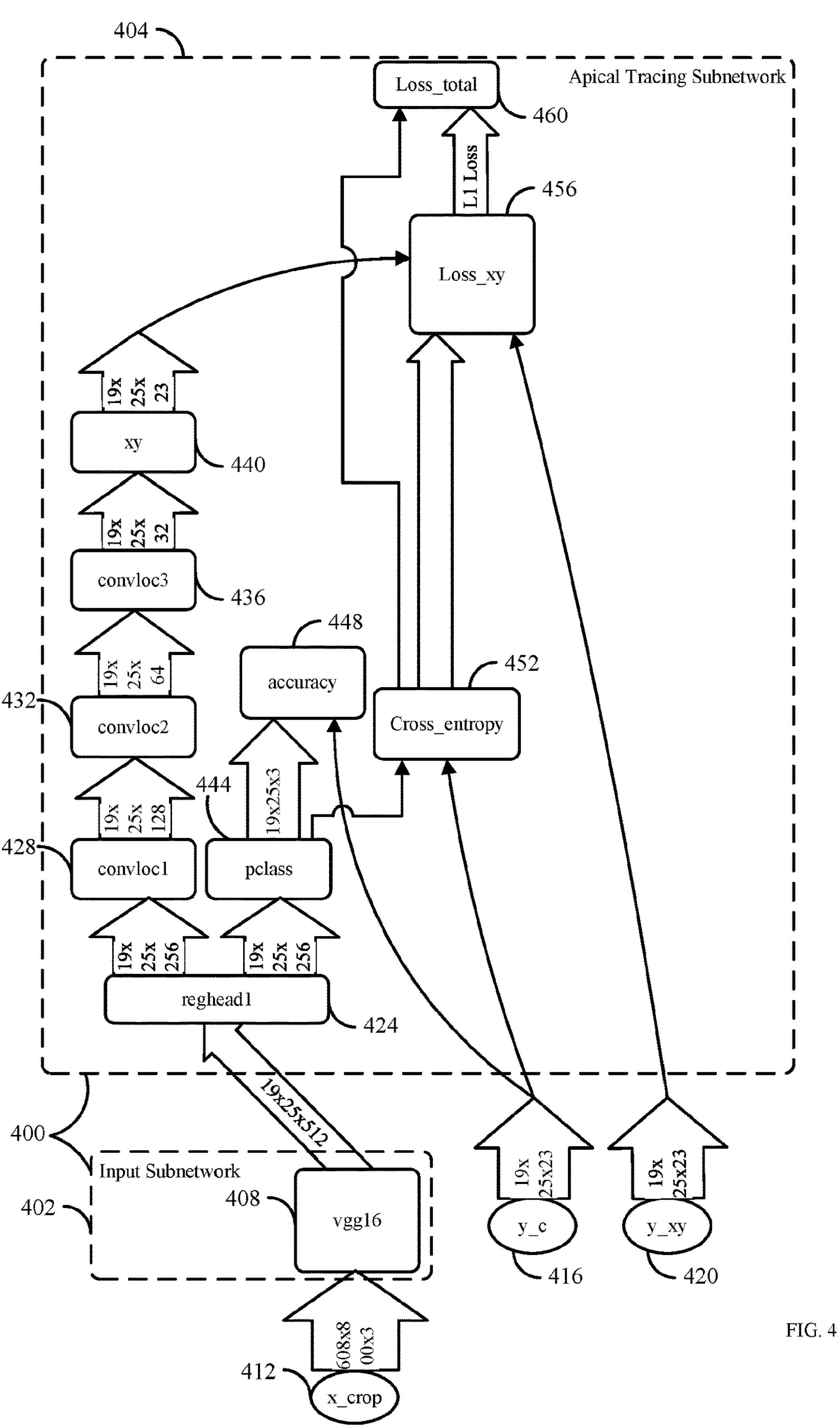
FIG. 4 is an example of a model for use with LVOTd detection in accordance with the present disclosure.

Referring now to FIG. 4, an example of a model 400 for LVOTd detection is shown. The model 400 can be a machine learning model. The model 400 can be an artificial neural network such as a convolutional neural network (CNN). In some configurations, the LV tracing detection and measurement 336 in FIG. 3 can provide an image frame from an apical view or a PLAX view (e.g., an image frame included in a DICOM® object associated with a PLAX view) to the model 400 and receive an indication of endpoints of the LVOTd in the apical or PLAX view, and by extension, a patient associated with the apical or PLAX view.

The model 400 can include an apical tracing subnetwork 404 and an input subnetwork 402. Generally, the input network 402 can receive an input image 412 and output a feature map of a predetermined size to the apical tracing subnetwork 404. In some configurations, the feature map can be 19×25×512 in size. The feature map may divide the input image into a grid (e.g., 19×25) and may include a vector features (e.g., 512 features for each grid cell).

In some configurations, the input subnetwork 402 can include a vgg16 network. The vgg16 network 408 can include a number of ReLu layers and MaxPool layers. In some configurations, the vgg16 network 408 can include the vgg16/conv1_1/Relu:0, vgg16/conv1_2/Relu:0, vgg16/pool1/MaxPool:0, vgg16/conv2_1/Relu:0, vgg16/conv2_2/Relu: 0, vgg16/pool2/MaxPool:0, vgg16/conv3_1/Relu:0, vgg16/conv3_2/Relu:0, vgg16/conv3_3/Relu:0, vgg16/pool3/MaxPool:0, vgg16/conv4_1.Relu:0, vgg16/con4_2/Relu:0, vgg16/conv4_3/Relu:0, vgg16/pool4/MaxPool:0, vgg16/conv5_1/Relu:0, vgg16/conv5_2/Relu:0, vgg16/conv5_3/Relu:0, and vgg16/pool5/MaxPool:0 listed in Table 1 below. The layers can cascade into each other in the order listed in the table below. The x_crop:0 layer can be the input image 412. In some configurations, the vgg16 network can be pre-trained.

TABLE 1

| Layer Name | Shape | Param # | Bytes | Trainable |
|---|---|---|---|---|
| x_crop:0 | (608, 800, 3) | 0 | 0 | False |
| vgg16/conv1_1/Relu:0 | (608, 800, 64) | 1792 | 7168 | False |
| vgg16/conv1_2/Relu:0 | (608, 800, 64) | 36928 | 147712 | False |
| vgg16/pool1/MaxPool:0 | (304, 400, 64 | 0 | 0 | False |

TABLE 1-continued

| Layer Name | Shape | Param # | Bytes | Trainable |
|---|---|---|---|---|
| vgg16/conv2_1/Relu:0 | (304, 400, 128) | 73856 | 295424 | False |
| vgg16/conv2_2/Relu:0 | (304, 400, 128) | 147584 | 590336 | False |
| vgg16/pool2/MaxPool:0 | (152, 200, 128) | 0 | 0 | False |
| vgg16/conv3_1/Relu:0 | (152, 200, 256) | 295168 | 1180672 | False |
| vgg16/conv3_2/Relu:0 | 152, 200, 256) | 590080 | 2360320 | False |
| vgg16/conv3_3/Relu:0 | (152, 200, 256) | 590080 | 2360320 | False |
| vgg16/pool3/MaxPool:0 | (76, 100, 256) | 0 | 0 | False |
| vgg16/conv4_1.Relu:0 | (76, 100, 512) | 1180160 | 4720640 | False |
| vgg16/con4_2/Relu:0 | (76, 100, 512) | 2359808 | 9439232 | False |
| vgg16/conv4_3/Relu:0 | (76, 100, 512) | 2359808 | 9439232 | False |
| vgg16/pool4/MaxPool:0 | (38, 50, 512) | 0 | 0 | False |
| vgg16/conv5_1/Relu:0 | (38, 50, 512) | 2359808 | 9439232 | False |
| vgg16/conv5_2/Relu:0 | (38, 50, 512) | 2359808 | 9439232 | False |
| vgg16/conv5_3/Relu:0 | (38, 50, 512) | 2359808 | 9439232 | False |
| vgg16/pool5/MaxPool:0 | (19, 25, 512) | 0 | 0 | False |
| LVOTdModel/reghead1/BiasAdd:0 | (19, 25, 256) | 1179904 | 4719616 | True |
| LVOTdModel/pclass/BiasAdd:0 | (19, 25, 3) | 6915 | 27660 | True |
| LVOTdModel/convloc1/BiasAdd:0 | (19, 25, 128) | 295040 | 1180160 | True |
| LVOTdModel/convloc2/BiasAdd:0 | (19, 25, 64) | 73792 | 295168 | True |
| LVOTdModel/convloc3/BiasAdd:0 | (19, 25, 32) | 18464 | 73856 | True |
| LVOTdModel/xy/BiasAdd:0 | (19, 25, 2) | 66 | 264 | True |

The apical tracing subnetwork 404 can include a reghead layer 424 (e.g., reghead1 in Table 1), a first convolutional layer 428 (e.g., convloc1 in Table 1), a second convolutional layer 432 (e.g., convloc2 in Table 1), a third convolutional layer 436 (e.g., convloc3 in Table 1) and an endpoint predictor layer 440 (e.g., xy in Table 1). The reghead layer 424, the first convolutional layer 428, the second convolutional layer 432, the third convolutional layer 436, and the endpoint predictor layer 440 can be trained and cascade into each other as shown in FIG. 4. The apical tracing subnetwork 404, and more specifically, the reghead layer 424, can receive the feature map output by the input subnetwork, and more specifically, the vgg16 subnetwork 408.

The endpoint predictor layer 440 can output an x coordinate and a y coordinate for each of the grid cells of the input image 412 as defined by the feature map output by the vgg16 subnetwork 408. In some configurations, the endpoint predictor layer 440 can output x and y coordinates for a 19×25 grid of cells. The x coordinate and y coordinate can represent a prediction of an endpoint, which may also be referred to as a keypoint, of the LVOTd of the patient. More specifically, the x coordinate and they coordinate can represent the location of a predicted endpoint within a cell. The predicted coordinates can be used along with predicted classifications for each grid cell to estimate the endpoints of the LVOTd and estimate the actual value of the LVOTd for the patient.

The apical tracing subnetwork 404 can include a grid classifier layer 444 (e.g., pclass in Table 1). The grid classifier layer 444 can receive the same output from the reghead layer 424 as the first convolutional layer 428. The grid classifier layer 444 can be trained to output a predicted classification for each grid cell. The classification can include whether the grid cell contains a first endpoint for the LVOTd, a second endpoint for the LVOTd, or is a background grid cell. The classification can be a three-dimensional vector where each dimension represents the likeliness that the cell contains the first endpoint, contains the second endpoint, or contains the background. Each dimension can include a non-zero value. The most likely classification can be associated with the largest value in the three-dimensional vector. Using the classifications output by the grid classifier layer, along with the predicted coordinates output by the endpoint predictor layer 440, the LVOTd can be estimated.

During training, the model 400 can receive ground truths associated with the input image 412 and reweight the reghead layer 424, the first convolutional layer 428, the second convolutional layer 432, the third convolutional layer 436, the endpoint predictor layer 440, and the grid classifier layer 444 using one or more equations. The ground truths can be generated by a human expert, such as a cardiologist. The ground truths can include a class location map 416 that can identify the classes associated with each grid cell. The class location map 416 should be all background cells except for a single cell containing the first endpoint and another cell containing the second endpoint. As one example, the class location map 416 can be 19×25×3, with the "3" representing a one-hot three dimensional vector. The ground truths can also include endpoint locations 420. The endpoint locations 420 can indicate where the first endpoint and the second endpoint are located within the grid. As one example, the endpoint locations 420 can be formatted as a 19×25×2 grid, where the correct endpoints are represented as x and y coordinates at the appropriate location in the 19×25 grid. However, in some configurations, the grids may be 19×25×N and 19×25×(1+N) for finding N points. The (1+N) configuration may be used for one-hot encoding when a single point can occupy a grid cell. The (N) configuration may be used for multi-hot encoding when multiple points may occupy each grid cell. As one example, in the case of apical processing, the 19×25×2 grid of the previous example may become 19×25×23 for the x, y estimation path and the 19×25×3 grid of the previous example may become 19×25×23 for the class probability (with 23 points in a multi-hot vector and all zeros encoding background).

During training, the model 400 can adjust weights based on a cross entropy calculation 452, an accuracy calculation 448, a coordinate loss calculation 456, and a total loss calculation 460. The total loss calculation 460 produces a total loss, which can be minimized during training. The total loss can be determined based on the accuracy calculation 448, which can be associated with classification accuracy, and based on the coordinate loss calculation 456, which can be associated with endpoint location accuracy. The cross entropy calculation 452 can calculate a cross entropy between the predicted classification for each grid cell generated by the grid classifier layer 444 and the class location map 416, which can act as the ground truth. The cross entropy calculation can include a weighted SoftMax cross entropy calculation. A weighted loss function, such as the weighted SoftMax cross entropy calculation, can be used in order to prevent the model 400 from labeling all pixels and/or grid cells as background due to the large number of background pixels in an input image.

The coordinate loss calculation 456 can calculate a L1 loss only for the grid cells that contain the true first endpoints and the true second endpoints. The coordinate loss calculation 456 can identify the grid cells that contain the true first endpoint and the true second endpoint based on the class location map and/or by the endpoints locations 420. The coordinate loss calculation 456 can calculate the L1 loss based on the coordinates of the true endpoints and the coordinates predicted at the corresponding grid cells by the endpoint predictor layer 440.

The total loss calculation 460 can receive the cross entropy calculated at the cross entropy calculation 452, as well as the L1 loss calculated at coordinate loss calculation 456, and calculate a total loss. In some configurations, the total loss can be the sum of the cross entropy and the L1 loss. Based on the total loss, the model 400, and more specifically the LVOTd subnetwork 404, can learn to identify endpoints and classify grid cells as containing the first endpoint, the second endpoint, or background. The total loss can be used to adjust weights in each layer of the apical tracing subnetwork 404.

Some existing networks use anchor boxes and multiple estimates per grid cell to obtain localization results for object detectors. This approach did not map well to the problem of identifying endpoints of an LVOTd in a patient. The present disclosure presents a new and superior approach to identifying the endpoints.

The model 400 can initially estimate the x and y coordinates for the endpoints as the center of each grid cell at the endpoint predictor layer 440. The apical tracing subnetwork 404 can then learn a small offset value to add to the initial value based on the cascade of the convolutional layers 428, 432, and 436. Thus, the x and y coordinates output by the endpoint predictor layer 440 can be the sum of the middle of the cell and the offset value. In some configurations, initial weights of the input subnetwork 402, can be set by pre-training the model 400 using the ImageNet dataset.

Figure 5:
FIG. 5 is an exemplary process for training the model of FIG. 4 in accordance with the present disclosure.
Figure 5:
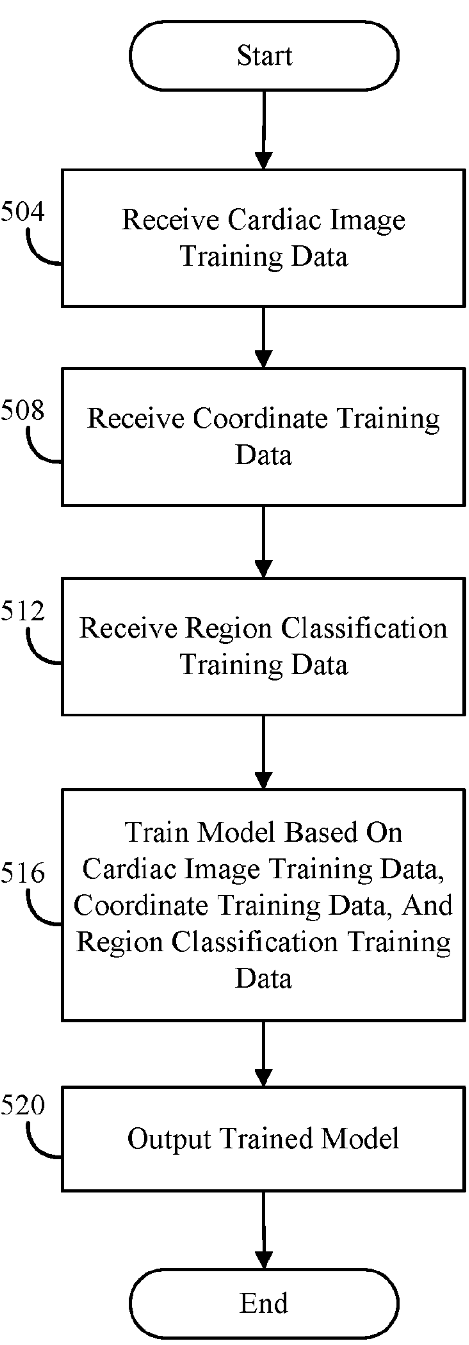

Referring now to FIG. 1 and FIG. 4 as well as FIG. 5, an exemplary process 500 for training the model 400 is shown. The process 500 can be used to train the model 400 to identify endpoints of an LVOTd as well as classify grid cells of an input cardiac image frame. The process 500 can be included in the cardiac image analysis application 140.

At 504, the process 500 can receive cardiac image training data. The cardiac image training data can include a number of echocardiogram images. More specifically, the cardiac image training data can include a number of image frames associated with a non-Doppler PLAX view. The image frames can be included one or more imaging objects such as DICOM® objects. The cardiac imaging training data may be included in the training data database 132.

At 508, the process 500 can receive coordinate training data associated with the cardiac image training data. For each image frame included in the cardiac image training data, the coordinate training data can include x,y coordinate values in a grid cell for a first endpoint, and x,y coordinate values in another grid cell for a second endpoint. The coordinate training data can be generated by a human expert, such as a cardiologist, labeling a first endpoint and a second endpoint of a LVOTd in each image frame included in the cardiac imaging training data. The raw coordinates (e.g., the actual coordinates in the input image) can be normalized to the coordinate location within a grid cell included in the image frame to produce the coordinate training data. The coordinate training data may be included in the training data database 132.

At 512, the process 512 can receive region classification training data associated with the cardiac image training data. For each image frame included in the cardiac image training data, the region classification training data can include a 19×25 grid of grid cells (or a different grid size depending on the network used in the input subnetwork), where each grid cell has an indicator of whether the grid cell contains the first endpoint, contains the second endpoint, or is a background cell for LVOTd measurements. For LVOTd, the indicator can be formatted as a three dimensional one-hot vector. Only one grid cell may be labeled as containing the first endpoint, and one grid cell may be labeled as containing the second endpoint. The remaining grid cells may be labeled as background cells. For apical tracings, the indicator can be formatted as a 23-dimensional multi-hot vector. In this configuration, a grid cell may be labeled as containing up to 23 points. A vector of zeros may be used to label grid cells that are background. The region classification training data can be generated by the human expert labeling grid cells of each image frame included in the cardiac image training data as containing the first endpoint, containing the second endpoint, or that the cell is a background cell. The region classification training data may be included in the training data database 132.

At 516, the process 500 can train the model 400 based on the cardiac image training data, the coordinate training data, and the region classification training data. For each image frame included in the cardiac image training data, the process 500 can provide the image frame to the model 400 as the input image 412, provide the portion of the coordinate training data associated with the image frame to the model 400 as the endpoint locations 420, and provide the portion of the region classification training data associated with the image frame to the model 400 as the class location map 416. The model 400 can then adjust weights based on the total loss calculated at the total loss calculation 460. At 520, the process 500 can output the model 400, which is now a trained model.

Figure 6:
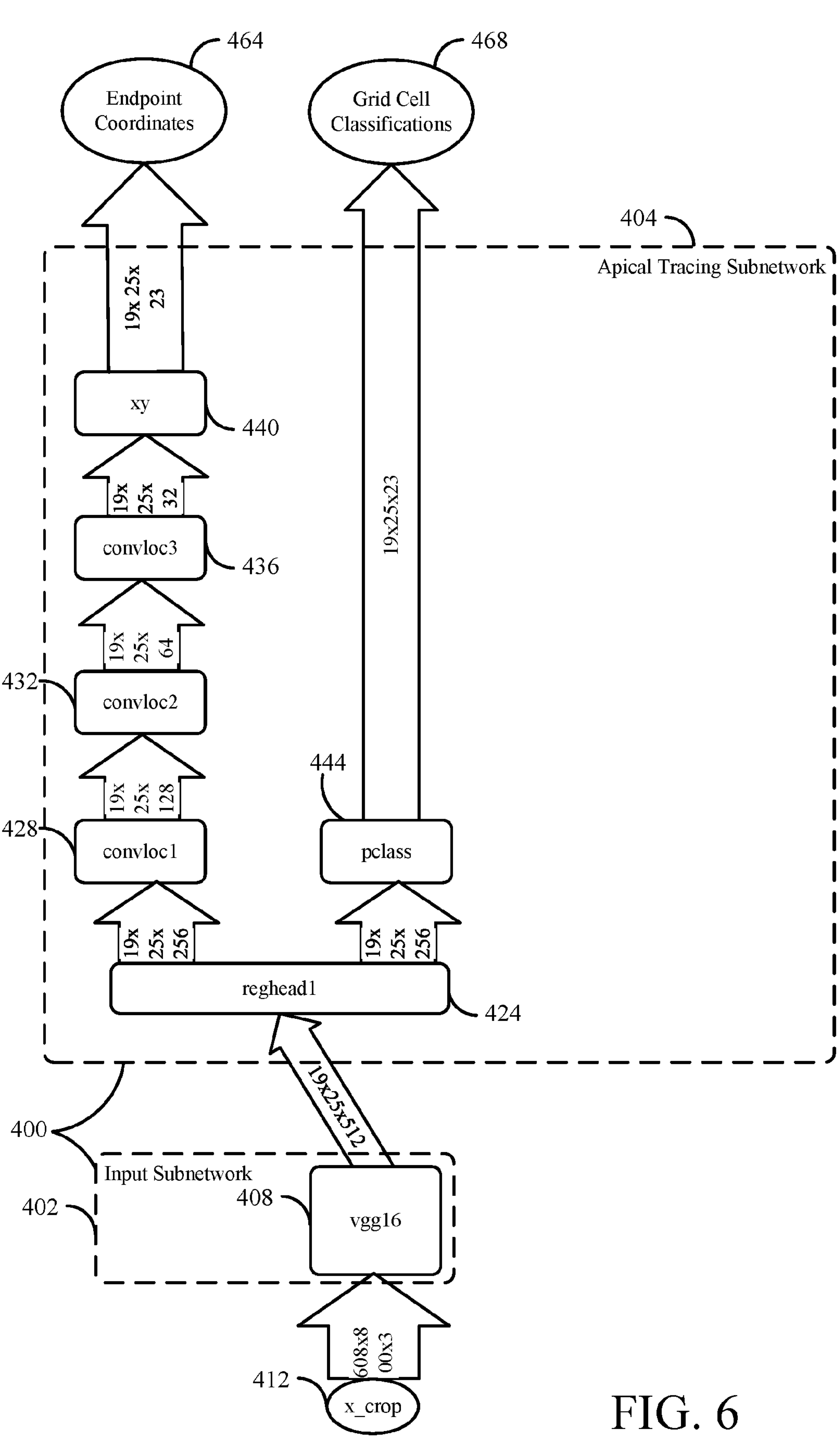
FIG. 6 is a trained version of the model of FIG. 4 in accordance with the present disclosure.

Referring to FIGS. 3, 4, and FIG. 5 as well as FIG. 6, a trained version of the model 400 is shown. The trained model 400 can be used in the LV tracing detection and measurement 336 in the flow 300 described above. After the model 400 is trained (e.g., using the process 500), the model does not need to use the entropy and/or loss calculations 452-460. The trained model 400 can include the input subnetwork 402, as well as the trained reghead layer 424, the trained first convolutional layer 428, the trained second convolutional layer 432, the trained third convolutional layer 436, the trained endpoint predictor layer 440, and the trained grid classifier layer 444.

The model 400 can receive the input image 412 (e.g., a PLAX view image frame) and output endpoint coordinates 464 and grid cell classifications 468 based on and associated with the input image 412. The endpoint predictor layer 440 can output the endpoint coordinates 464 for each grid cell. The endpoint coordinates 464 can include an x coordinate and a y coordinate associated with each grid cell. The grid classifier 444 can output the grid cell classifications 468 including a classification for each grid cell as described above. The classification for each grid cell can include three values (e.g., a three-dimensional vector) that indicate the likeliness the grid cell contains the first endpoint, the second endpoint, or background pixels. Each of the three values may be non-zero value. The actual value of the LVOTd can be estimated based on the endpoint coordinates 464 and the grid cell classifications 468.

The LV tracing detection and measurement 336 can include determining an actual size (e.g., size in mm) of the LVOTd based on the output endpoint coordinates 464 and the grid cell classifications 468. The LV tracing detection and measurement 336 may determine which grid cell has the highest score (e.g., value in a three-dimensional vector) for the first endpoint, and which grid cell has the highest score for the second endpoint. The LV tracing detection and measurement 336 may select the coordinates included in the endpoint coordinates 464 associated with the grid cell that has the highest score for the first endpoint, and scale the coordinates back to the original input image 412. The LV tracing detection and measurement 336 may select the coordinates included in the endpoint coordinates 464 associated with the grid cell that has the highest score for the second endpoint, and scale the coordinates back to the original input image 412. Using the scaled back endpoints for the first and second endpoints along with metadata about the original sizing of the input image 412 (e.g., metadata extracted at the metadata extraction 312), the process can determine the length (e.g., in mm) between the coordinates associated with the first and second endpoints. The LVOTd can be estimated to be the length between the coordinates associated with the first and second endpoints.

Figure 7:
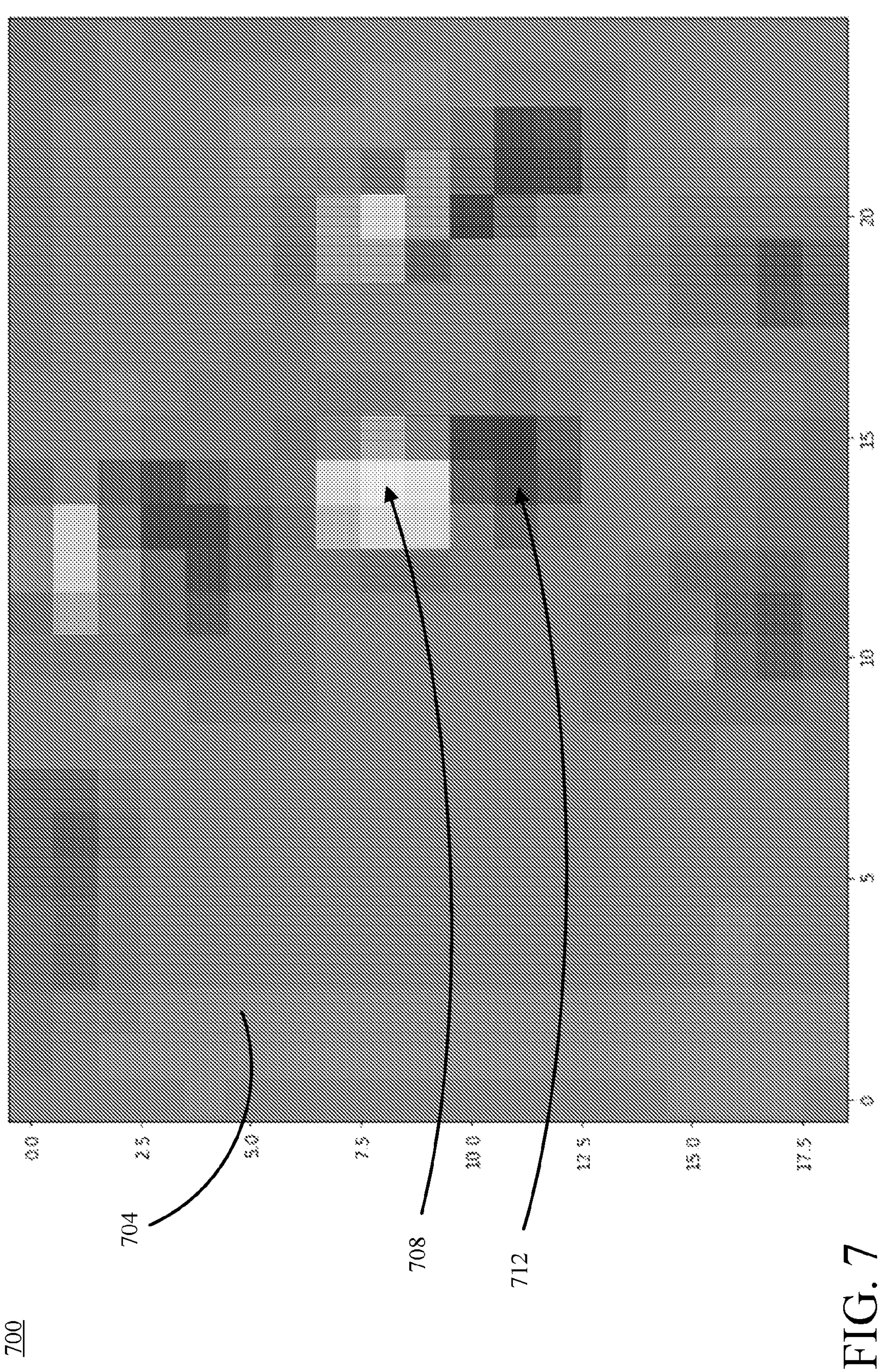
FIG. 7 is an exemplary visual representation of grid cell classifications in accordance with the present disclosure.

Referring now to FIGS. 3 and 6 as well as FIG. 7, an exemplary visual representation of grid cell classifications 700 is shown. The grid cell classifications 700 can be the grid cell classification 468 output by the model 400. The visual representation of the grid cell classifications 700 can be included in a report, such as a report generated at the report generation 360 in the flow 300.

The grid cell classifications 700 can be visually represented by varying the color of each grid cell based on the classification scores for the first endpoint, the second endpoint, and background. In some configurations, the color of each cell can be generated by setting pixels in the grid cell equal to an RGB value based on the classification scores. The classification scores can be normalized (e.g., normalized to range between zero and one). The red value can be set based on the score for the background. For example, for a normalized background score of zero, the red value can be set to zero, while for a normalized background score of one, the red level can be set to a maximum red level (e.g., 255 in an eight bit system). The green level can be set based on the normalized second endpoint score in similar fashion. The blue level can be set based on the normalized second endpoint score in similar fashion.

The grid cell classifications 700 can include a number of background grid cells 704, as well as a first endpoint grid cell 708 and a second endpoint grid cell 712. The first endpoint grid cell 708 and the second endpoint grid cell 712 can be the grid cells with the highest first endpoint score and the highest second endpoint score, respectively.

Figure 8:
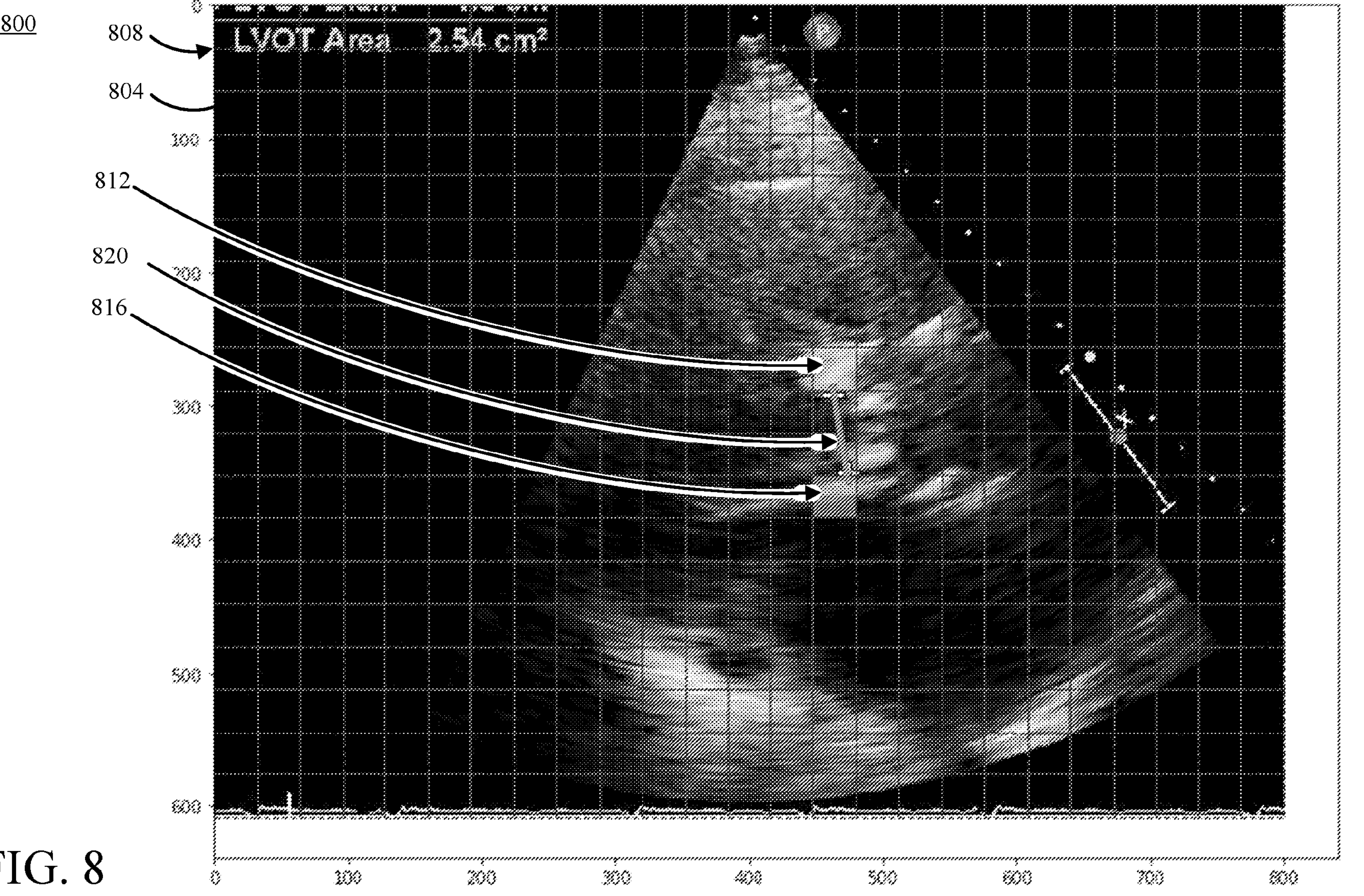
FIG. 8 is an exemplary annotated image frame in accordance with the present disclosure.

Referring now to FIGS. 3, 6, and 7 as well as FIG. 8, an exemplary annotated image frame 800 is shown. The annotated image frame 800 can be associated with the grid cell classifications 700 in FIG. 7. The annotated image frame 800 can include a PLAX view image frame 804, a grid 808 overlaid on the PLAX view image frame 804, a first visual indicator 812 associated with a grid cell that includes a first endpoint of an LVOTd, a second visual indicator 816 associated with a grid cell that includes a second endpoint of the LVOTd, and a third visual indicator 820 associated with the LVOTd. The PLAX view image frame 804 can be a raw image frame (e.g., a JPEG file).

The first visual indicator 812 and the second visual indicator 816 can each include a color and/or pattern that may distinguish the associated grid cells from surrounding grid cells. The first visual indicator 812 can be associated with the first endpoint grid cell 708, and second visual indicator 816 can be associated with the second endpoint grid cell 712. The third visual indicator can include a line representing the LVOTd. The line can be a straight or substantially straight line extending between the first endpoint and the second endpoint. The annotated image frame 800 can be included in a report, such as a report generated at the report generation 360 in the flow 300.

Figure 9:
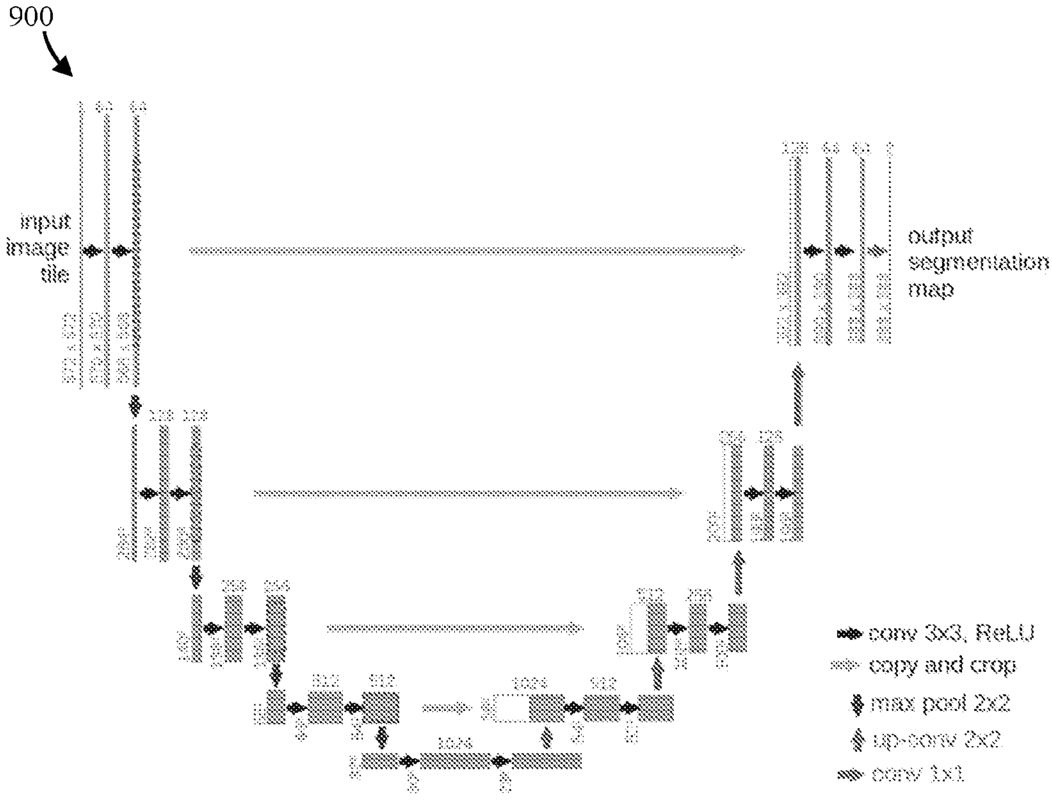
FIG. 9 is a model for identifying information about a VTI envelope in a Doppler profile image frame in accordance with the present disclosure.

Referring now to FIG. 3 as well as FIG. 9, a model 900 for identifying information about a VTI envelope in a Doppler profile image frame is shown. The model 900 can mark pixels included in a VTI envelope for PW Doppler profile image frames and/or CW profile Doppler image frames. In some configurations, the model 900 can be trained to mark pixels included in VTI envelopes for both PW Doppler profile image frames and CW Doppler profile image frames. The model 900 can include a number of layers. In some configurations, the layers can cascade into each other via 3×3 ReLU filters, 2×2 max pool layers, copy and crop transformations, and 2×2 upconvolutional filters, and 1×1 convolutional filters. In some configurations, the model 900 can be a modified version of the UNet model described by Ronneberger, et al. in the "U-net: Convolutional Networks For Biomedical Image Segmentation" (2015) paper, which is fully incorporated herein by reference. In some configurations, the model 900 can be the UNet model modified to receive input sizes associated with echocardiogram data and fine-tuned using layers with weights selected for Doppler data. The model 900 can receive a Doppler profile image frame and output a number of marked pixels associated with the Doppler profile image frame. Using hand labeled envelopes to define truth label masks, the model 900 can learn to produce per pixel predictions that define whether or not a source pixel included in the input image belongs to VTI the envelope mask. Pixel-wise cross entropy can be used to define the loss function that is minimized by the back-propagation algorithm.

Figure 10:
FIG. 10 is a process for training the model of FIG. 9 in accordance with the present disclosure.
Figure 10:
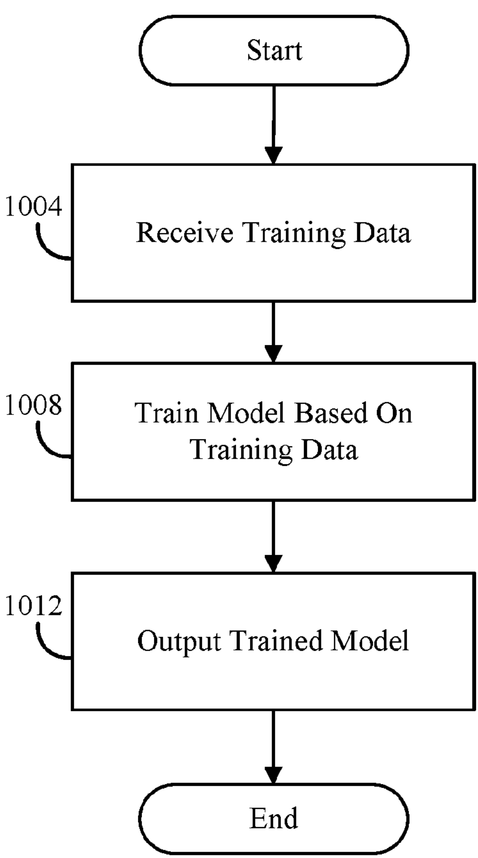

Referring now to FIGS. 3 and 9 as well as FIG. 10, a process 1000 for training the model 900 is shown. The process 1000 can be used to train the model 900 to mark pixels included in a VTI envelope for a PW Doppler profile image frame or a CW Doppler profile image frame. The process 1000 can be included in the cardiac image analysis application 140.

At 1004, the process 1000 can receive training data. The training data can include a number of Doppler profile image frames annotated by an expert, such as a cardiologist. The annotated image frames can include marked pixels (e.g., marked by the expert) that are included in the VTI envelope. The training data may be included in the training data database 132.

At 1008, the process 1000 can train the model 900 based on the training data. The process 1000 can sequentially provide the annotated image frames to the model 900.

At 1012, the process 1000 can output the model 900, which is now a trained model.

Figure 11:
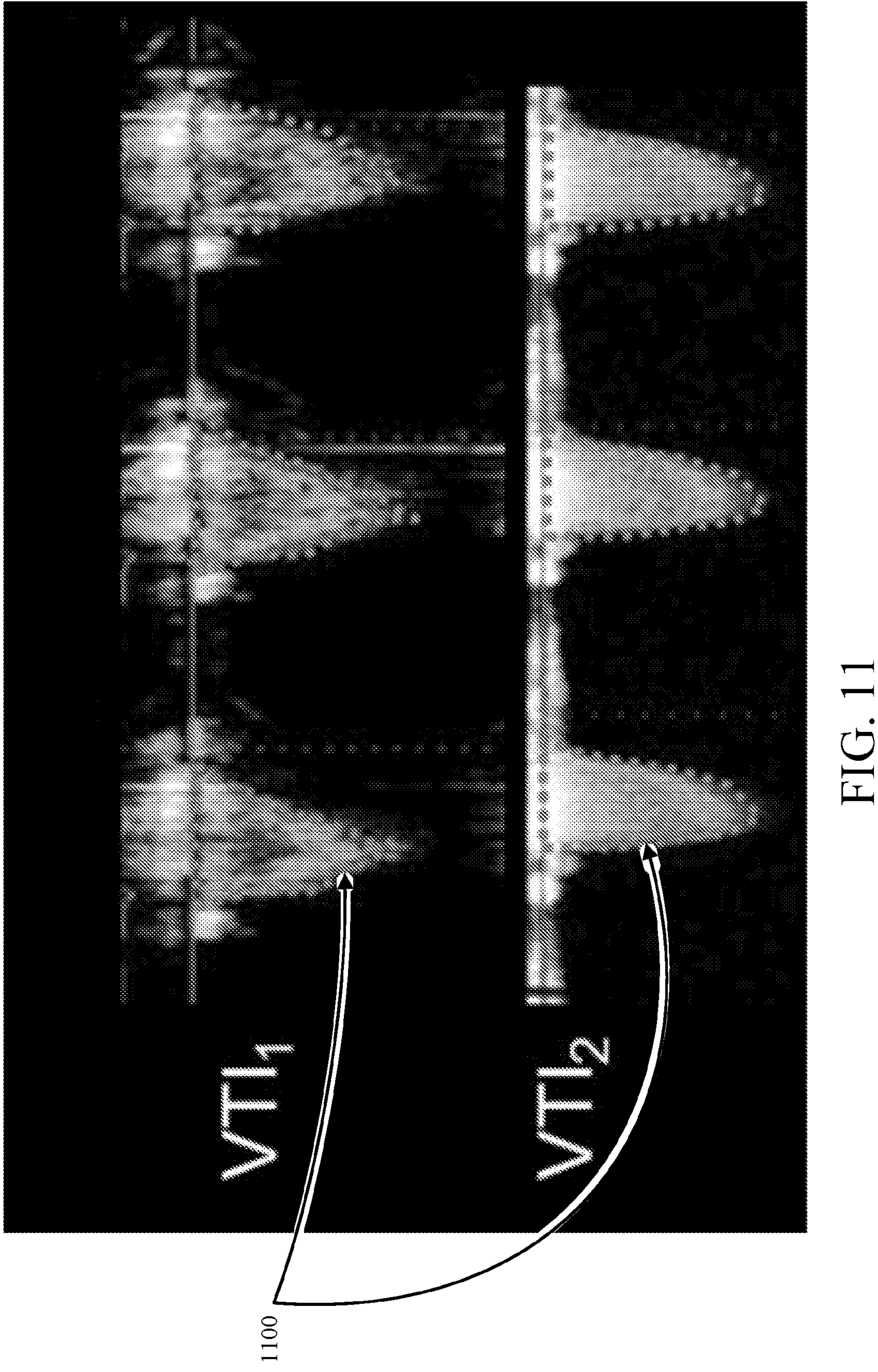
FIG. 11 is exemplary marked pixels overlaid on Doppler profile image frames in accordance with the present disclosure.

FIG. 11 shows exemplary marked pixels 1100 overlaid on Doppler profile image frames. The marked pixels 1100 can outline VTI envelopes for PW VTI envelopes ($VTI_1$ in the top row) and CW VTI envelopes ($VTI_2$ in the bottom row). The marked pixels 1100 may be generated and output by the model 900 in FIG. 9, or be annotations from an expert, such as a cardiologist. In other words, the marked pixels can be predictions from the model 900 or included in training data used to train the model 900.

Figure 12:
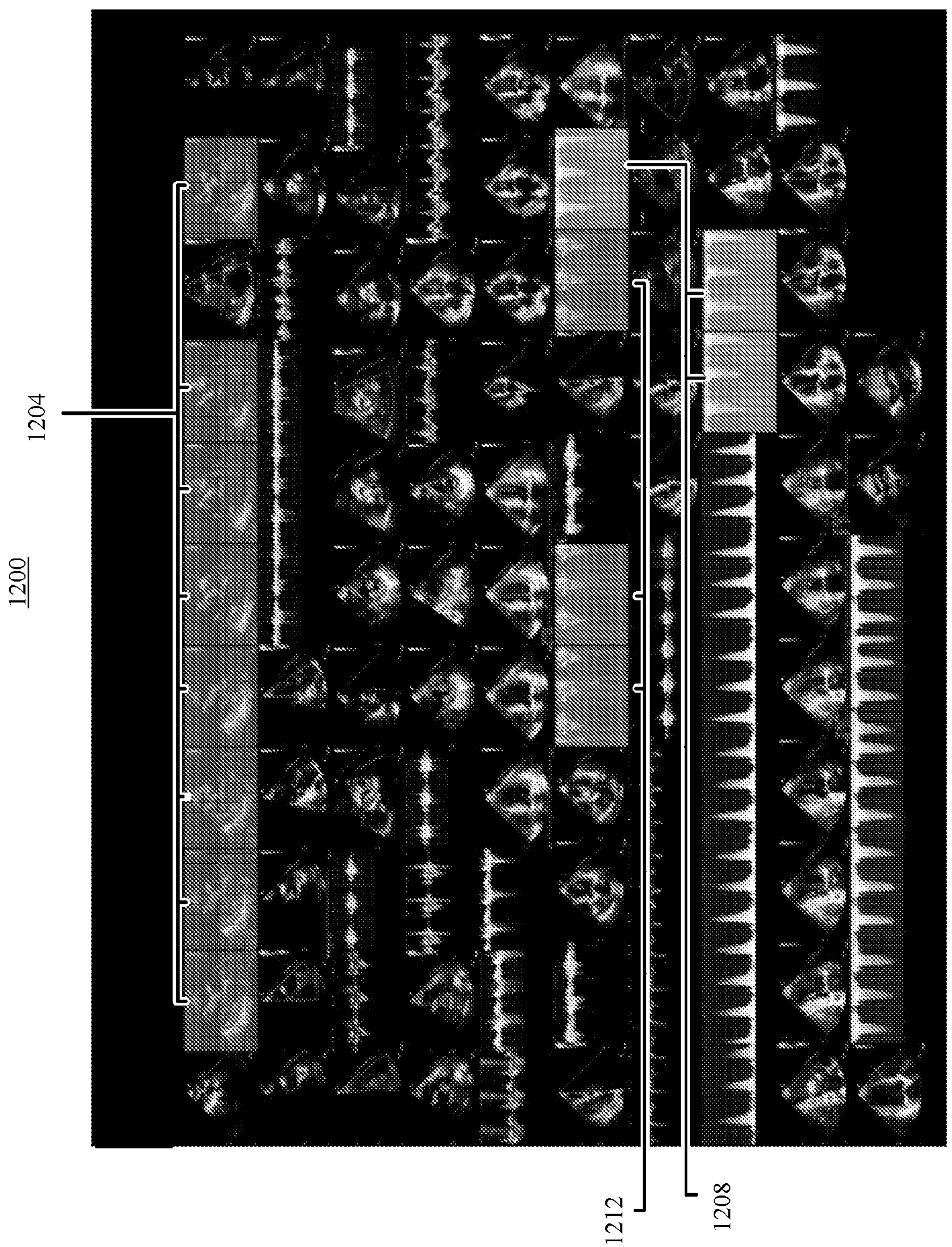
FIG. 12 is an example of cardiac image data in accordance with the present disclosure.

FIG. 12 shows an example of cardiac image data 1200. The cardiac image data 1200 can include transthoracic echocardiogram data associated with a patient, and may be formatted in the DICOM® standard. In some configurations, the cardiac image 1200 can include a plurality of imaging objects, such as DICOM® objects, that each include one or more image frames.

FIG. 12 illustrates the large amount of imaging data that can be associated with a patient, and how most of the data is not relevant for calculating AVA. Out of over one hundred image frames in FIG. 12, only fourteen may be used for calculating AVA. As shown, the cardiac image data 1200 can include eight PLAX view image frames 1204, three CW Doppler profile image frames 1208, and three PW Doppler profile image frames 1212.

The cardiac image analysis flow 300 and/or the cardiac image analysis application 140 can receive the cardiac image data 1200 and determine the relevant views for and calculate AVA and/or other metrics such as mean pressure gradient, maximum pressure gradient, and other metrics described above. The cardiac image analysis flow 300 and/or the cardiac image analysis application 140 can significantly reduce the burden on practitioners, such as cardiologists, in analyzing the large amount of data in the cardiac images data 1200.

Figure 13:
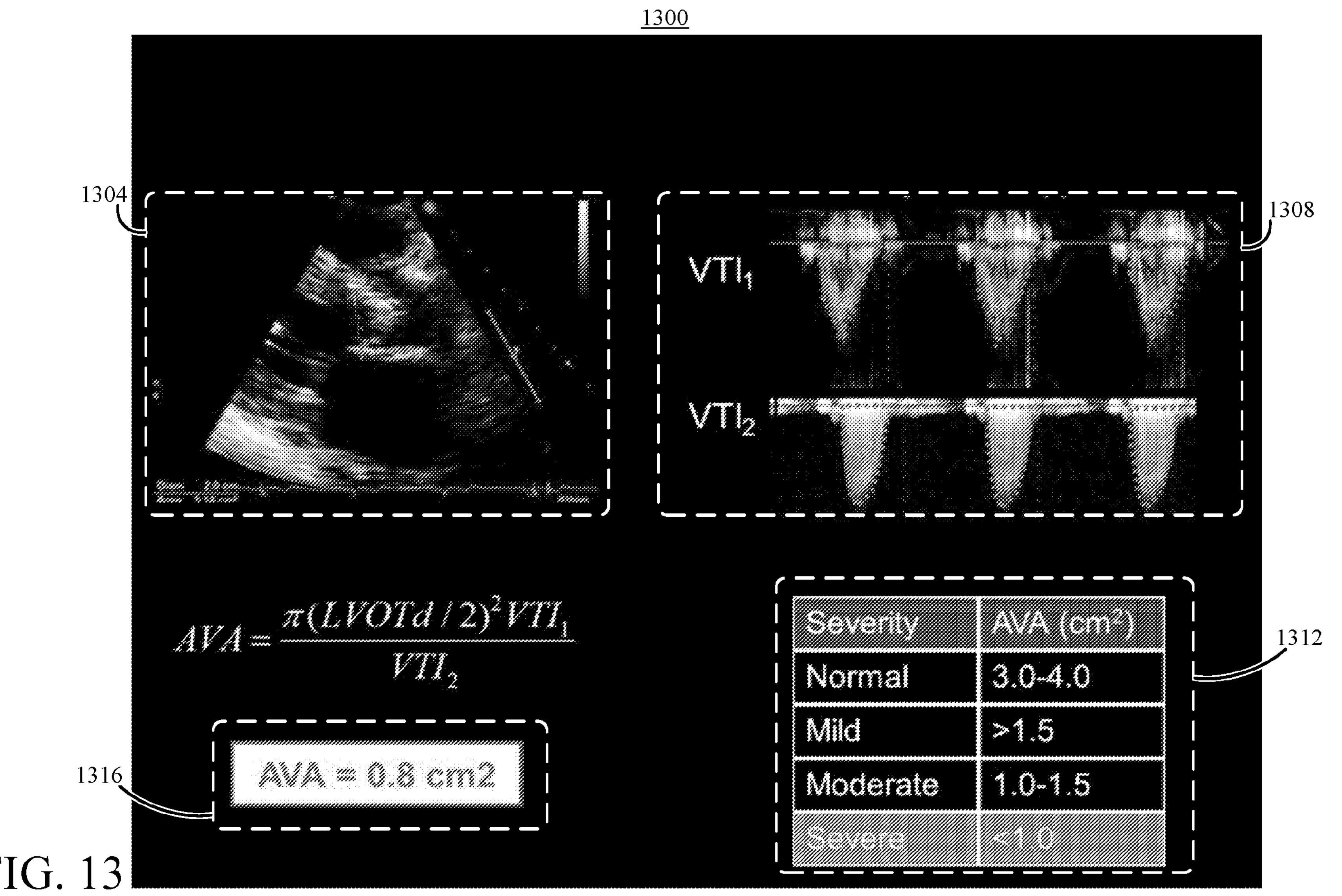
FIG. 13 is an exemplary report associated with a patient in accordance with the present disclosure.

Referring now to FIGS. 3 and 13 as well as FIG. 13, an exemplary report 1300 associated with a patient is shown. The report 1300 can be generated at the report generation 360 in the flow 300. The report 1300 can include an annotated PLAX image frame 1304 including an indication of the LVOTd (e.g., the third indicator 820 in FIG. 8). The report 1300 can include one or more Doppler view image frames 1308 (e.g., PW Doppler and/or CW Doppler view image frames) that may include annotations such as marked pixels (e.g., marked pixels 1100 in FIG. 11). The report 1300 can include a raw AVA 1316 calculated for the patient and/or a table 1312 or other ranking indicator that displays a severity category that the patient falls in accordance with the raw AVA 1316.

Figure 14:
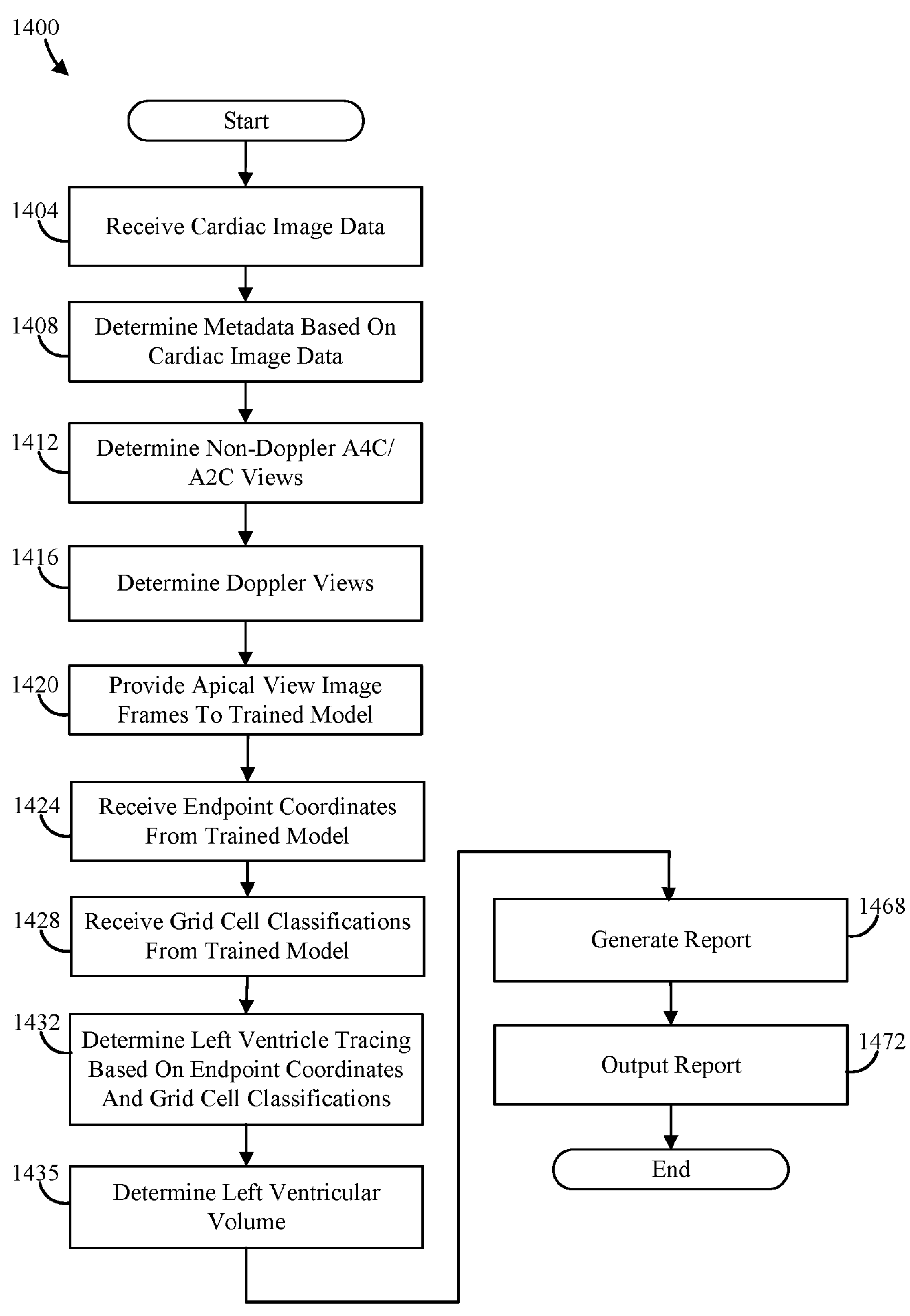
FIG. 14 is an exemplary process for automatically analyzing cardiac image data in accordance with the present disclosure.

Referring now to FIGS. 1 and 3, 6, 9, and 13 as well as FIG. 14, an exemplary process 1400 for automatically analyzing cardiac image data, such as echocardiogram data, is shown. The cardiac imaging data can include a number of imaging objects, such as DICOM® imaging objects, that may each contain one or more images image frames. The cardiac image analysis application 140 can include the process 1400.

At 1404, the process 1400 can receive cardiac image data. At least a portion of the cardiac image data can include transthoracic echocardiogram data. The cardiac image data can be formatted in a DICOM® standard.

At 1408, the process 1400 can determine metadata based on the cardiac image data. The process 1400 may extract metadata including parameters such as patient age binned into age ranges following HIPAA rules, BMI, heart rate, image size, number of image frames (e.g., the number of image frames in the image data), units in the image frames (e.g., the scale of each image frame), whether or not the data (e.g., the imaging object) contains Doppler tracings (e.g., true or false), whether or not the image was a thumbnail view, the location of the image frames within the sequence of images taken during the study (e.g., the image frames were the sixth and seventh images generated, respectively), image scaling data, and other data suitable for analyzing cardiac image data. In some configurations, the metadata can be extracted from attributes (i.e., fields) included in the imaging objects as described above for the metadata extraction 312.

At 1412, the process 1400 can determine non-Doppler views, including apical views, such as Apical 4 chamber (A4C) and Apical 2 chamber (A2C) views, included in the cardiac image data. The process 1400 can determine which imaging objects and/or image frames included in the cardiac image data are non-Doppler A4C/A2C views based on the metadata determined at 1408, which may indicate whether or not the data (e.g., the imaging object) contains Doppler tracings (e.g., true or false). In some configurations, the process 1400 may provide non-Doppler views to a trained classifier, such as a CNN, and receiving an indication of whether or not each non-Doppler view is an A4C view or an A2C view. The process 1400 may provide the non-Doppler A4C/A2C views identified by the trained classifier to a trained classifier such as a CNN, and receiving a quality metric for each view. The quality metric may indicate a level of confidence that the view is a suitable view of the LVOTd. The process 1400 may filter out views with quality metrics below a predetermined threshold. In some configurations, the process 1400 may implement at least a portion of the view sorting 324, the heart view classification 328, and/or the A4C/A2C subtype classification 332 described above. Alternatively or in addition, in some configurations, block 1412 is performed with respect to PLAX views (e.g., non-Doppler PLAX views).

At 1416, the process 1400 can determine Doppler views included in the cardiac image data. The process 1400 can determine which imaging objects and/or image frames included in the cardiac image data are Doppler views based on the metadata determined at 1408, which may indicate whether or not the data (e.g., the imaging object) contains Doppler tracings (e.g., true or false). The process 1400 can also determine if the view is a PW Doppler view or a CW Doppler view. In some configurations, the process 1400 may implement at least a portion of the view sorting 324 and/or Doppler classification 340 described above.

At 1420, the process 1400 can sequentially provide image frames associated with the views identified at 1412 to a trained model (e.g., the A4C/A2C views, the PLAX views, etc.). In some configurations, the trained model can be the trained model 400 described above in conjunction with FIG. 6. For each image frame included in the imaging objects and/or image frames associated with the A4C/A2C views, the process 1400 can provide the image frame to the model 400 as the input image 412. The trained model can divide each image frame into a grid of cells (i.e., grid cells).

At 1424, the process 1400 can receive a number of endpoint coordinates from the trained model. The endpoint coordinates can be associated with the image frames associated with the PLAX views. For each image frame input (e.g., as the input image 412), the process 1400 can receive endpoint coordinates (e.g., the endpoint coordinates 464) for each image frame. The endpoint coordinates can include coordinates for the first endpoint and the second endpoint of an LVOTd in the image frame. Each set of coordinates can be associated with a grid cell as described above.

At 1428, the process 1400 can receive a number of grid cell classifications from the trained model. The grid cell classifications can be associated with the image frames associated with the views and/or the endpoint coordinates (e.g., A4C/A2C views or PLAX views). For each image frame input, the process 1400 can receive grid cell classifications (e.g., the grid cell classifications 468) for each image frame. The grid cell classifications can include a classification for each grid cell as described above. The classification for each grid cell can include three values (e.g., a three-dimensional vector) that indicate the likeliness the grid cell contains the first endpoint, the second endpoint, or background pixels. Each of the three values may be non-zero value.

At 1432, the process 1400 can determine left ventricle tracing for each image frame associated with the A4C/A2C views based on the endpoint coordinates and grid cell classifications. For each image frame, the process 1400 may select the coordinates included in the endpoint coordinates that are associated with the grid cell that has the highest score for the first endpoint, and scale the coordinates back to the original size of the image frame.

The process 1400 may select the coordinates included in the endpoint coordinates that are associated with the grid cell that has the highest score for the second endpoint, and scale the coordinates back to the original input image 412.

Using the scaled back endpoints for the first and second endpoints along with metadata about the original sizing of the image frame (e.g., metadata determined at 1408), the process can determine the length (e.g., in mm) between the coordinates associated with the first and second endpoints. For example, LVOTd can be estimated to be the length between the coordinates associated with the first and second endpoints. The process 1400 may average the LVOTd determined for each image frame, and use the averaged LVOTd as a "final" LVOTd in an AVA calculation. In some configurations, the process 1400 may implement at least a portion of the LVOTd detection and measurement 336 include in the flow 300.

In some configurations, the process 1400 can sequentially provide image frames associated with the PW Doppler views identified at 1416 to a trained model. In some configurations, the trained model can be the trained model 900 described above in conjunction with FIG. 9. For each image frame included in the imaging objects and/or image frames associated with the PW Doppler views, the process 1400 can provide the image frame to the model 900.

The process 1400 can receive a number of PW VTI outline indications from the trained model. Each PW VTI outline indication can be associated with an image frame and include a number of marked pixels (e.g., the marked pixels 1100). The marked pixels can indicate pixels that are included in a VTI envelope.

The process 1400 can determine a PW VTI value based on the PW VTI outline indications. For each PW VTI outline indication, the process 1400 may determine the Doppler envelope segmentation using a morphological operation. The morphological operation can determine the Doppler envelope segmentation based on marked pixels included in the outline indication. The process 1400 can determine a PW VTI based on the Doppler envelope segmentation and scaling information associated with the image frame (e.g., one pixel is one millimeter in length). The process 1400 may average the PW VTI obtained for each image frame and/or PW Doppler view. The averaged PW VTI can be a "final" PW VTI that can be used in the AVA equation. However, it is appreciated that the final PW VTI can be the raw PW VTI determined for a single image frame. The process 1400 may implement at least a portion of the PW/CW Doppler VTI calculation 348 included in the flow 300.

The process 1400 can sequentially provide image frames associated with the CW Doppler views identified at 1416 to a trained model. In some configurations, the trained model can be the trained model 900 described above in conjunction with FIG. 9. For each image frame included in the imaging objects and/or image frames associated with the CW Doppler views, the process 1400 can provide the image frame to the model 900.

The process 1400 can receive a number of CW VTI outline indications from the trained model. Each CW VTI outline indication can be associated with an image frame and include a number of marked pixels (e.g., the marked pixels 1100). The marked pixels can indicate pixels that are included in a VTI envelope.

The process 1400 can determine a CW VTI value based on the CW VTI outline indications. For each CW VTI outline indication, the process 1400 may determine the Doppler envelope segmentation using a morphological operation. The morphological operation can determine the Doppler envelope segmentation based on marked pixels included in the outline indication. The process 1400 can determine a CW VTI based on the Doppler envelope segmentation and scaling information associated with the image frame (e.g., one pixel is one millimeter in length). The process 1400 may average the CW VTI obtained for each image frame and/or CW Doppler view. The averaged v VTI can be a "final" v VTI that can be used in the AVA equation. However, it is appreciated that the final CW VTI can be the raw CW VTI determined for a single image frame. The process 1400 may implement at least a portion of the PW/CW Doppler VTI calculation 348 included in the flow 300.

The process 1400 can calculate AVA based on the PW VTI, the CW VTI, and the LVOTd. The PW VTI can be the final PW VTI determined at 1444. The CW VTI can be the final CW VTI. The LVOTd can be the final LVOTD. The process 1400 can calculate the AVA using equation (1) as described above.

The process 1400 can determine maximum pressure gradient and/or mean pressure gradient based on the Doppler views. In some configurations, the process 1400 can implement at least a portion of the peak and mean pressure gradient calculation 356 in the flow 300.

At 1435, the process 1400 can compute left ventricular volume. The processor 1400 may determine the left ventricular volume based using a clinical practice, such as, e.g., Simpson method and/or Simpson Biplane method, as described above.

At 1468, the process 1400 can generate a report based on ejection fraction, the AVA, the mean pressure gradient, the maximum pressure gradient, the LVOTd, the PW VTI, and/or the CW VTI. In some configurations, the report can include an annotated PLAX image frame (e.g., the annotated PLAX image frame 1304), one or more Doppler view image frames (e.g., the Doppler view image frames 1308), the raw AVA (e.g., the raw AVA 1316), and/or a table (e.g., the table 1312) or other ranking indicator that displays a severity category that the patient falls in accordance with the raw AVA.

At 1472, the process 1400 can output the report to at least one of a memory or a display. In some configurations, at 1472, the process 1400 can cause the report to be displayed on a display (e.g., the display 108).

It is understood that at least some of the steps included in the process 1400 can be rearranged and/or executed in parallel.

The cardiac image analysis application 140 can include the process 500 in FIG. 5, the process 1000 in FIG. 10, and/or the process 1400 in FIG. 14. The processes 500, 1000, and 1400 may be implemented as computer readable instructions on a memory or other storage medium and executed by a processor.

Thus, the present disclosure provides systems and methods for automatically analyzing echocardiogram data.

The present invention has been described in terms of one or more preferred embodiments, and it should be appreciated that many equivalents, alternatives, variations, and modifications, aside from those expressly stated, are possible and within the scope of the invention.

The invention claimed is:

1. A cardiac image analysis system comprising at least one processor and at least one memory, the cardiac image analysis system configured to:

receive cardiac image data associated with a patient;

determine apical chamber image frames included in the cardiac image data;

provide the apical chamber image frames to a trained model;

receive tracing coordinates from the trained model;

receive grid cell classifications from the trained model;

determine a change in left ventricular volume for apical chambers of the patient based on the tracing coordinates and the grid cell classifications;

determine ejection fraction for the patient based on the change in left ventricular volume for the apical chambers of the patient; and determine an aortic valve area for the patient by:

providing a pulsed-wave Doppler image frame to a second trained model;

receiving an outline indication from the second trained model; and determining a first velocity time integral based on the outline indication, wherein the aortic valve area for the patient is based on the first velocity time integral.

2. The system of claim 1, wherein the cardiac image data includes echocardiogram data.

3. The system of claim 2, wherein the echocardiogram data is transthoracic echocardiogram data.

4. The system of claim 1, wherein the system is configured to determine a left ventricular outflow tract diameter for an image frame included in the cardiac image data by:

extracting metadata associated with the image frame from the cardiac image data;

determining a first grid cell associated with the image frame contains a first endpoint based on the grid cell classifications;

determining a second grid cell associated with the image frame contains a second endpoint based on the grid cell classifications; and determining the left ventricular outflow tract diameter based on coordinates associated with the first grid cell and included in the endpoint coordinates, coordinates associated with the second grid cell and included in the endpoint coordinates, and the metadata.

5. The system of claim 4, wherein the grid cell classifications are associated with a number of grid cells that divide the image frame, and wherein each grid cell classification comprises a first value that indicates the likeliness that a target grid cell contains the first endpoint, a second value that indicates the likeliness that the target grid cell contains the second endpoint, and a third value that indicates the likeliness that the target grid cell contains background pixels.

6. The system of claim 4, wherein the trained model comprises a first subnetwork comprising a convolutional neural network and a second subnetwork comprising another convolutional neural network.

7. The system of claim 1, wherein the grid cell classifications are associated with a number of grid cells that divide the image frame, and wherein each grid cell classification comprises a set of values, wherein each value indicates a likeliness that a target grid cell contains at least one endpoint and another value that indicates a likeliness that the target grid cell contains background pixels.

8. The system of claim 1, wherein the system is configured to determine an aortic valve area for the patient by:

providing a continuous-wave Doppler image frame to a second trained model;

receiving an outline indication from the second trained model; and determining a second velocity time integral based on the outline indication, wherein the aortic valve area for the patient is based on the second velocity time integral.

9. The system of claim 1, wherein the system is further configured to:

generate a report based on the ejection fraction; and cause the report to be displayed.

10. A cardiac image analysis method comprising:

receiving cardiac image data associated with a patient;

determining apical chamber image frames included in the cardiac image data;

providing the apical chamber image frames to a trained model;

receiving tracing coordinates from the trained model;

receiving grid cell classifications from the trained model;

determining a change in left ventricular volume for apical chambers of the patient based on the tracing coordinates and the grid cell classifications;

determining ejection fraction for the patient based on the change in left ventricular volume for the apical chambers of the patient; and determining an aortic valve area for the patient by:

providing a pulsed-wave Doppler image frame to a second trained model;

receiving an outline indication from the second trained model; and determining a first velocity time integral based on the outline indication, wherein the aortic valve area for the patient is based on the first velocity time integral.

11. The method of claim 10, wherein the cardiac image data includes echocardiogram data.

12. The method of claim 11, wherein the echocardiogram data includes at least one of transthoracic echo data, transesophageal echo data, or echocardiogram data.

13. The method of claim 10, further comprising determining a left ventricular outflow tract diameter for an image frame included in the cardiac image data by extracting metadata associated with the image frame from the cardiac image data;

determining a first grid cell associated with the image frame contains a first endpoint based on the grid cell classifications;

determining a second grid cell associated with the image frame contains a second endpoint based on the grid cell classifications; and determining the left ventricular outflow tract diameter based on coordinates associated with the first grid cell and included in the tracing coordinates, coordinates associated with the second grid cell and included in the tracing coordinates, and the metadata.

14. The method of claim 13, wherein the grid cell classifications are associated with a number of grid cells that divide the image frame, and wherein each grid cell classification comprises a first value that indicates the likeliness that a target grid cell contains the first endpoint, a second value that indicates the likeliness that the target grid cell contains the second endpoint, and a third value that indicates the likeliness that the target grid cell contains background pixels.

15. The method of claim 13, wherein the trained model comprises a first subnetwork comprising a vgg16 convolutional neural network and a second subnetwork comprising another convolutional neural network.

16. The method of claim 10, further comprising determining an aortic valve area for the patient by:

providing a continuous-wave Doppler image frame to a second trained model;

receiving an outline indication from the second trained model; and determining a second velocity time integral based on the outline indication, wherein the aortic valve area for the patient is based on the second velocity time integral.

17. The method of claim 10, wherein the method further comprises:

generating a report based on the ejection fraction; and causing the report to be displayed.

18. An image analysis method comprising:

receiving cardiac image data associated with a patient;

determining image frames with predetermined anatomical information from the cardiac image data;

providing the image frames with the predetermined anatomical information to a trained model; and determining an aortic valve area for the patient by:

providing a pulsed-wave Doppler image frame to a second trained model;

receiving an outline indication from the second trained model; and determining a first velocity time integral based on the outline indication, wherein the aortic valve area for the patient is based on the first velocity time integral.

* * * * *